United States Patent
Ribault et al.

(10) Patent No.: US 7,482,155 B1
(45) Date of Patent: Jan. 27, 2009

(54) CHIMERIC PROMOTERS FOR CONTROLLING EXPRESSION IN SMOOTH MUSCLE CELLS

(75) Inventors: Sébastien Ribault, Plan de Cuques (FR); Pascal Neuville, La Wantzenau (FR); Majid Mehtali, The Hague (NL)

(73) Assignee: Transgene S.A., Strasbourg (FR)

( * ) Notice: Subject to any disclaimer, the term of this patent is extended or adjusted under 35 U.S.C. 154(b) by 1093 days.

(21) Appl. No.: 10/312,963

(22) PCT Filed: Jul. 4, 2001

(86) PCT No.: PCT/EP01/07657

§ 371 (c)(1), (2), (4) Date: Dec. 31, 2002

(87) PCT Pub. No.: WO02/02765

PCT Pub. Date: Jan. 10, 2002

(30) Foreign Application Priority Data

Jul. 5, 2000 (EP) .............................. 00440208.7

(51) Int. Cl.
- *C12N 15/63* (2006.01)
- *A61K 48/00* (2006.01)
- *C07H 21/04* (2006.01)

(52) U.S. Cl. ................. 435/320.1; 514/44; 536/24.1

(58) Field of Classification Search .............. 800/8; 435/320.1, 91.1, 455, 320.19; 514/44; 536/24.1
See application file for complete search history.

(56) References Cited

U.S. PATENT DOCUMENTS

2002/0152486 A1* 10/2002 Paulin et al.

FOREIGN PATENT DOCUMENTS

| WO | WO9936101 | * | 7/1999 |
| WO | WO 00/18908 | | 4/2000 |
| WO | WO0202765 | * | 1/2002 |

OTHER PUBLICATIONS

Barnhart et al, Enhancer and promoter Chimeras in Plasmids Designed for Intramuscular Injection: A Comparative In Vivo and In Vitro Study, Human Gene Therapy, 9:2545-2553,1998.*
Ribault et al, Circulation Research, 88: 468-475, Feb. 2001.*
Kallmeier et al, JBC, 270(52): 30949-30957, 1995.*
Barnhart et al, Human Gene Therapy, 9: 2545-2553, 1998.*
Verma et al, Nature, 389: 239-242, 1997.*
Romano et al, Stem Cells, 18: 19-39, 2000.*
Pfeifer et al, Annu Rev Genomics Hum Genet, 2: 177-211, 2001.*
Krasnykh et al, Molecular Therapy, 1(2): 391-405, 2000.*
Strauch et al, Emerging Therapeutics Targets, 3(2): 279-306, 1999.*
Trask et al. (J. Biol. Chem., vol. 263, pp. 17142-17149, 1988.*
Li et al, (Nature Biotechnology, 17: 241-245, 1999.*
Chamberlain et al. (WO 98/17783.*
Jaynes et al. (Mol. Cel. Biol., vol. 6, pp. 2855-2864, 1986.*
Gldspink et al, (WO 98/49333, filed (Nov. 5, 1998).*
Yamamura Hisako et al; "Structure and expression of the human SM22-alpha gene, assignment of the gene to chromosome 1, and repression of the promoter activity by cytosine DNA methylation"; Journal of Biochemistry, vol. 122, No. 1, 1997, pp. 157-167.
Agah Ramtin et al; "Cardiovascular overexpression of transforming growth factor-betal causes abnormal yolk sac vasculogenesis and early embryonic death", Circulation Research, vol. 86, No. 10, May 26, 2000, pp. 1024-1030.
Ribault Sebastien et al; "Chimeric smooth muscle-specific enhancer/promoters: Valuable tools for adenovirus-mediated cardiovascular gene therapy", Circulation Research, vo. 88, No. 5, Mar. 16, 2001, pp. 468-475.
Ribault S et al; "Potential use of chimeric smooth muscle specific promoters in restenosis", Journal of Submicroscopic Cytology and Pathology, vol. 32, No. 3, Jul. 2000, p. 468.

* cited by examiner

*Primary Examiner*—Anne-Marie Falk
*Assistant Examiner*—Magdalene K Sgagias
(74) *Attorney, Agent, or Firm*—Buchanan, Ingersoll & Rooney, P.C.

(57) ABSTRACT

The present invention concerns a chimeric construct comprising a SMC-specific promoter operably linked to a muscle-specific enhancer. It also provides an expression cassette comprising such a chimeric construct to control expression of a therapeutic gene. Finally, the invention relates to a recombinant vector, a viral particle, an eukaryotic host cell, a composition comprising said expression cassette and their use for specific expression in SMCs and for therapeutic or prophylactic purposes, a method for the treatment of a human or animal organism as well as a transgenic non-human animal comprising integrated into its genome the chimeric construct, the expression cassette or the vector of the present invention.

16 Claims, 4 Drawing Sheets

CHIMERIC PROMOTERS FOR CONTROLLING EXPRESSION IN SMOOTH MUSCLE CELLS

Figure 1:
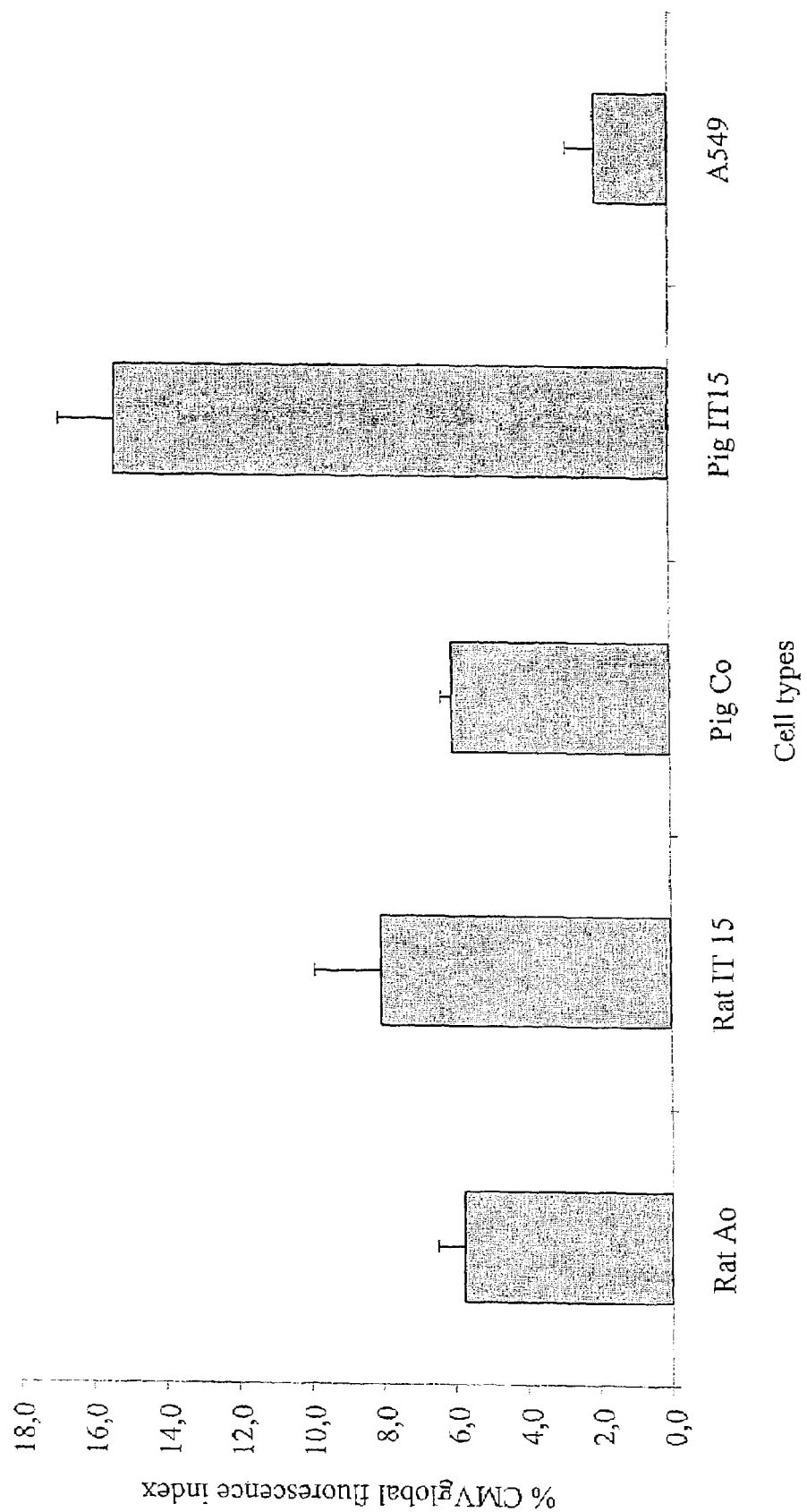

The present invention concerns a chimeric construct comprising a smooth-muscle cell (SMC)-specific promoter operably linked to a muscle-specific enhancer. It also provides an expression cassette comprising such a chimeric construct to control expression of a therapeutic gene. Finally, the invention relates to a recombinant vector, a viral particle, a eukaryotic host cell, a pharmaceutical composition comprising said expression cassette and their use for specific expression in smooth muscle cells and for therapeutic or prophylactic purposes as well as a transgenic animal having incorporated in its genome said expression cassette. The present invention relates to the field of tissue-specific gene expression and is useful for many applications including the production of recombinant polypeptides in cultured cell lines, the construction of transgenic animal models, the study of gene regulation and the development of vascular targeting technologies. It is of very special interest in relation to gene therapy, especially in the cardiovascular field.

Gene therapy can be defined as the transfer of genetic material into a cell or an organism. The possibility of treating human disorders by gene therapy has changed in a few years from the stage of theoretical considerations to that of clinical applications. The first protocol applied to man was initiated in the USA in September 1990 on a patient who was genetically immunodeficient as a result of a mutation affecting the gene encoding adenine deaminase (ADA) and the relative success of this first experiment encouraged the development of the technology for various genetic and acquired diseases. Promising clinical trials based on gene therapy are currently ongoing (see for example clinical trials listed at www.wiley.co.uk/genetherapy/clinical).

Cardiovascular diseases represent a major target for gene therapy approaches since they are the leading cause of mortality in most of the industrialized countries. The capacity of smooth muscle cells (SMCs) to proliferate and modulate their phenotype has been implicated in the pathogenesis of a number of diseases including atherosclerosis, restenosis and asthma. To illustrate, injury of the arterial wall induces the synthesis of cytokines and other growth-regulatory molecules that stimulate SMC migration and proliferation, leading to intimal hyperplasia (Ross, 1993, Nature 362, 801-809), which contributes to the onset of several cardiovascular disorders, including atherosclerosis. A common and clinically significant setting for such injury is balloon angioplasty where the occlusive artery is dilated mechanically with a balloon on a catheter to restore blood flow. However, in 30 to 50% of the cases, a reactive cellular proliferation response leads to regrowth of smooth muscle cells locally that compromises blood circulation (Schwartz et al., 1996, Int. J. Cardiol. 53, 71-80). This process called restenosis has been refractory to conventional approach. Thus, gene transfer into SMCs holds promise both for elucidating the pathogenesis of these cardiovascular diseases and for their treatment by gene therapy.

Successful gene therapy depends principally on the efficient delivery of the therapeutic gene to the cells of a living organism and the expression of the genetic information. Functional genes can be introduced into cells by a variety of techniques resulting in either transient expression or permanent transformation of the host cells with incorporation of said genes into the host genome. Whereas naked nucleic acids (i.e. plasmid DNA) can be used for carrying the genes of interest into target cells (Wolff et al., 1990, Science 247, 1465-1468), the majority of the gene therapy protocols uses viral or synthetic vectors.

Viruses have developed diverse and highly sophisticated mechanisms to achieve transport across the cellular membrane, to escape from lysosomal degradation, for delivery of their genome to the nucleus and, consequently, have been used in many gene delivery applications. While those derived from retroviruses and adenoviruses have been extensively used (for reviews, see Crystal, 1995, Science 270, 404-410; Kovesdi et al., 1997, Curr. Opinion Biotechnol 8, 583-589; Miller, 1997, Human Gene Ther. 8, 803-815), other viral vectors such as poxvirus-derived vectors, are emerging as promising candidates for in vivo gene transfer.

Synthetic vectors refer to special combination of nucleic acid (e.g. plasmid DNA) with lipids or polymers which facilitate its cellular uptake. Various lipids and polymers-based vectors are currently available (for a review, see for example Rolland, 1998, Critical reviews in Therapeutic Drug Carrier Systems 15, 143-198). Although less efficient than viral vectors, the synthetic vectors present potential advantages with respect to large-scale production, safety, low immunogenicity and cloning capacity.

However, the broad host range of the present gene therapy vectors can represent a major limitation for their use. This lack of specificity could lead to a widespread expression of the therapeutic genes which might be harmful to the patient, especially when cytotoxic genes are transferred. Thus, means for restricting gene expression to a targeted category of cells would be useful in gene therapy.

Several investigators have proposed to modify vector specificity by attaching ligands which specifically bind to target cell-surface polypeptides (Roux et al., 1989, Proc. Natl. Acad Sci. USA 86, 9079-9083; WO94/10323). For example, Goud et al. (1988, Virol. 163, 251-254) linked anti-transferrin receptor antibodies to the retroviral envelope protein to obtain delivery of the retrovirus particle to human cells bearing the transferrin receptor. However, while binding and internalization occurred, infection and replication did not. Moreover, this technology is complex and, to be specific, needs to abrogate the existing interactions between the vector and its naturally occurring cellular receptor.

Another alternative is to restrict gene expression to a desired cell population by using tissue-specific transcriptional regulatory elements. Two major DNA sequences are required for the complete and efficient regulation of gene transcription in mammalian cells: i.e the promoter and the enhancer. The promoter is located immediately upstream (5') from the initiation site of the transcription (cap site or +1) and is required for accurate and efficient initiation of the transcription from the initiation site. The majority of the eukaryotic promoters includes specific cis-acting sequences, for example (i) an AT rich region called TATA box present approximately 30 base pairs 5' to the cap site and required for determining the cap site and initiating gene transcription (Breathnach and Chambon, 1981, Ann. Rev. Biochem. 50, 349-380), and (ii) one or more upstream promoter elements (UPEs) that increase the efficiency of transcription initiation and are required for a promoter to function at an adequate level (Gene VI, 1997, Initiation of transcription p 810-846, Ed B. Lewin, Oxford University Press). These cis-acting sequences are recognized and bound by nuclear transcriptional factors that either are ubiquitous (found in any cell type) or have a regulatory role (synthetized or activated at specific times or in specific tissues).

The activity of promoters is additionally modulated by other sequences called <<enhancers>>, which may increase the rate of transcription from the promoter. The components of enhancers resemble those of the promoters, since they also contain several cis-acting sequences recognized by transcriptional factors but these sequences are organized in a more closely packed array. These cis-acting sequences of enhancers are also recognized and bound by nuclear transcriptional factors that either are ubiquitous (e.g. viral enhancers) or have a regulatory role (targets for tissue-specific or temporally regulated transcriptional factors). An enhancer may be located over distances of up to several kilobase pairs (kb) from the promoter, either upstream or downstream of it and in either orientation (Gene VI, 1997, Initiation of transcription p 810-846, Ed B. Lewin, Oxford University Press).

Numerous tissue-specific promoters/enhancers have been described in the literature that allow the specific and selective expression of genes in various tissues (for a review, see Maniatis et al., 1987, Science 236, 1237-1245; Fickett et al., 2000, Current Opinion in Biotechnology 11, 19-24). However, only a few SMC-specific promoters/enhancers have been identified so far. Examples are limited to those of smooth muscle α-actin (Foster et al., 1992, J. Biol. Chem. 267, 11995-12003; Shimizu et al., 1995, J. Biol. Chem 270, 7631-7643), smooth muscle myosin heavy chain (SM-MHC) (Katoh et al., 1994, J. Biol. Chem 269, 30538-30545), desmin (European application EP 0 999 278; Mericskay et al., 1999, Current Topics in Pathology Vol 93 p 7-17; Eds Desmoulière and Tuchweber, Springer-Verlag Berlin Heidelberg) and SM22α, genes (Duband et al., 1993, Differentiation 55, 1-11).

The SM22α promoter is functional in all smooth muscle tissues (visceral as well as vascular SMCs). The 445 base pairs (bp) immediately upstream of the transcription initiation site are sufficient to program gene expression in a SMC lineage-restricted fashion, in visceral and vascular SMCs, as shown in cultured SMCs (Solway et al., 1995, J. Biol. Chem. 270, 13460-13469; Kim et al., 1997, J. Clin. Invest. 100, 1006-1018; U.S. Pat. No. 6,015,711) as well as in vivo in transgenic mice (Li et al., 1996, J. Cell Biol. 132, 849-859; Moessler et al., 1996, Development 122, 2415-2425) and by intraarterial administration (Kim et al., 1997, J. Clin. Invest. 100, 1006-1018). Moreover, the far upstream region of the SM22α gene has been shown to contain other transcriptionnally regulated cis-acting sequences which display a specificity of expression restricted to arterial SMCs and more especially aorta (WO97/35974), illustrating the complexity of the transcriptional activity of the SM22α gene.

However, if the precited transcriptional elements are properly regulated in a SMC restricted fashion, they are usually weak and provide expression levels much lower (10 to 200 fold) than those obtained with <<strong>> promoters/enhancers, such as those of Cytomegalovirus (CMV; Boshart et al., 1985, Cell 41, 521-530) or other viruses. However, such viral transcriptional elements are usually non-specific, being active in a wide variety of cell types from many species.

Chimeric constructs combining CMV or skeletal muscle-specific enhancers with skeletal muscle-specific promoters have been described in the literature (Barnhart et al., 1998, Human Gene Ther. 9, 2545-2553). While some associations significantly enhance the expression level of the luciferase reporter gene in cultured differentiated skeletal muscle cells (compared to enhancer-less constructs), strong expression is also observed in non-muscle BHK cells, reaching up to 100% of the expression level obtained with the CMV promoter/enhancer. Moreover, some chimeric constructs exhibiting strong enhancement in vitro, do not reproduce such an increase in vivo when injected in skeletal muscles. As mentioned by Barnhart et al., the critical parameters that define gene expression are complex, depending on the nature, number, orientation and position of the enhancer relative to the promoter sequence as well as the sequence environment.

Chimeric constructs associating the CMV enhancer with SMC-specific promoters, including the SM22α promoter, have been recently described in WO00/18908. Transfection studies of various cultured cell lines demonstrate activation of gene expression in SMCs when the CMV enhancer is present. However, the chimeric constructs also retain a strong inducibility in non SMCs, reaching up to 26% of the expression level obtained with the strong CMV promoter/enhancer used as control. Such a background expression in non targeted cells may be incompatible with human gene therapy, especially when delivery of cytotoxic genes is envisaged.

Altogether, these studies make clear that it is difficult to design an appropriate promoter/enhancer combination allowing significant levels of gene expression while retaining a restricted specificity to target cells and, preferably, to SMCs.

Therefore, there is still a need in the art to design transcriptional elements leading to high level and specific expression of genes in SMCs, especially in the SMCs of the vasculature, in order to achieve therapeutic levels of protein expression and to avoid the potential side effects inherent to a widespread gene expression.

This technical problem is solved by the provision of the embodiments as defined in the claims.

Accordingly, the present invention provides a chimeric construct comprising at least (i) a smooth muscle cell (SMC)-specific promoter operably linked with at least (ii) a muscle-specific enhancer.

The term <<chimeric construct >> as used herein refers to a nucleic acid construct comprising at least two sequences of various origins referring to species, genes etc. Preferably, these two sequences, i.e. the SMC-specific promoter and the muscle-specific enhancer, are heterologous to each other, i.e. they originate from different genes or from different species, more preferably they are heterologous in the sense that they originate from different genes and from different species. Within the present invention, the terms <<nucleic acid>> and <<polynucleotide>> are used interchangeably and define a polymeric form of any length of nucleotides or analogs thereof. The term <<polynucleotide>> includes any possible nucleic acid, in particular DNA which can be single or double stranded, linear or circular, natural or synthetic. A polynucleotide may comprise modified nucleotides, such as methylated nucleotides and nucleotide analogs (see U.S. Pat. No. 5,525,711, U.S. Pat. No. 4,711,955 or EPA 302 175 as examples of modifications). Such a polynucleotide can be obtained from existing nucleic acid sources (e.g. genomic, cDNA) but can also be synthetic (e.g. produced by oligonucleotide synthesis). The sequence of nucleotides may be interrupted by non-nucleotide elements. A polynucleotide may be further modified after polymerization.

The nucleotide positions referenced in the present application for the SMC-specific promoter and the muscle-specific enhancer are numbered negatively relative to the transcription initiation site or cap site (representing position +1). The first nucleotide directly upstream from the transcription initiation site is numbered −1. The initiation site of transcription can be determined by standard techniques such as S1 mapping or primer extension (Sambrook et al., 1989, Laboratory Manual, Cold Spring Harbor Laboratory Press, Cold Spring Harbor N.Y.).

The term <<smooth muscle cell (SMC)>> refers to any type of smooth muscle cell including visceral and vascular SMCs and more especially arterial SMCs, with a special preference for neointimal and medial SMCs of aorta, coronary, mammary, femoral and carotid arteries as well as of saphenous vein.

The term "SMC-specific promoter" as used herein means any nucleic acid sequence recognized by transcription factor(s) and/or RNA polymerase present in a smooth muscle cell, thereby promoting expression of an adjacent gene. The term "adjacent gene" refers to genes, the transcription of which is controlled by said promoter and/or the chimeric construct of the invention. In particular, the term "specific" means that the promoter in use in the present invention and/or the chimeric construct of the invention shows a propensity to direct gene expression in SMCs, whereas in non-SMCs, it is not at all or not very active (reduced activity of at least a factor 5, preferably at least 10).

The SMC-specific promoter used in the present invention, encompasses at least all the elements necessary to promote gene expression even at low levels in SMCs. Such a promoter may be a so-called "minimal promoter" which includes the cis-acting sequences necessary to allow RNA polymerase binding site and to initiate transcription at the cap site, such as a TATA box (consensus sequence TATAAAA) or a TATA box-like element (an AT rich sequence having a TATA box function), preferably located 25-35 bp of the cap site. The presence of a TATA box can be determined by sequence analysis whereas the initiation site of transcription can be determined by standard techniques, such as S1 mapping or primer extension. A minimal SMC-specific promoter is usually comprised within a 200 base pairs (bp) fragment, advantageously, within a 100 base pairs (bp) fragment 5' (upstream) to the transcription initiation site.

According to a second and preferred alternative, the chimeric construct of the present invention employs a SMC-specific promoter containing additional cis-acting sequences which allow to substantially increase gene expression directed by a minimal promoter in SMCs. Such cis-acting sequences may be bound by transcriptional factors, either ubiquitous or having a regulatory role (temporal or tissue-specific), especially SMC-specific factors. Representative examples include without limitation CAAT box (consensus GGCCAATCT) bound by NF-1 factor, GC box (consensus GGGCGG) bound by SP1 factor, octamer ATTTGCAT bound by Oct factor, 6B (consensus GGGACTTTCC) bound fy NF6B, ATF (consensus GTGACGT) bound by ATF factor Ap2, Sp1, Egr1, YY1, TGT3-3, E box (CANNTG), CarG box (CC(A/T)$_6$GG) and/or MEF-2 (YTAWAAATAR) sequences. These cis-acting sequences may be used alone or in various combinations and may be homologous (isolated from the SMC-specific promoter in use in the present invention) or heterologous (isolated from another promoter region). In this context, it may be advantageous to fuse different portions of several SMC-specific promoters in order to optimize gene expression in SMCs.

According to this preferred embodiment, a SMC-specific promoter in use in the chimeric construct of the invention is contained within a 4000 bp fragment, advantageously within a 2000 bp fragment, preferably within a 1000 bp fragment and, more preferably within a 500 bp fragment upstream of the transcription initiation site.

Furthermore, the SMC-specific promoter in use in the chimeric construct of the present invention may comprise a transcription initiation site functional in the targeted SMCs, if not present in the adjacent gene.

According to a preferred embodiment, the SMC-specific promoter used in the chimeric construct of the invention is selected from the group consisting of the promoters of smooth muscle α-actin (Foster et al., 1992, J. Biol. Chem. 267, 11995-12003 Shimizu et al., 1995, J. Biol. Chem 270, 7631-7643), smooth muscle myosin heavy chain (SM-MHC) (Katoh et al., 1994, J. Biol. Chem 269, 30538-30545), smooth muscle calponin (Miano et al., 1996, J. Biol. Chem. 271, 7095-7103 for the mouse gene; Nobrega et al., 2000, Mamm Genome 11, 115-119 for the rat gene and Kitami et al., 1999, Hypertens. Res. 22, 187-193 for the human gene), desmin (European application EP 0 999 278; Mericskay et al., 1999, Current Topics in Pathology Vol 93 p 7-17; Eds Desmoulière and Tuchweber, Springer-Verlag Berlin Heidelberg) and SM22α genes (Duband et al., 1993, Differentiation 55, 1-11). The use of a SM22α promoter is preferred. Within the scope of this preferred embodiment are 5' deleted fragments of these promoters that are still capable of mediating SMC-specific expression.

The chimeric construct of the present invention may employ a SM22α promoter from any species, and in particular from human, mouse, rat, hamster, rabbit, pig. The sequence of the SM22α promoter of various species is accessible to the man skilled in the art from literature or specialized data banks (such as Genebank under accession numbers AH006172.1 for the human sequence, Z.68618.1 for the mouse sequence and Z48607.1 for the rat sequence). The position of the key cis-acting sequences can be determined on the basis of the published data.

The SM22α promoter of the mouse gene is particularly preferred in the context of the present invention, and especially the portion of the mouse SM22α promoter comprised within a 445 bp fragment upstream of the transcription initiation site (i.e. in SEQ ID NO: 1 from positions 1 to 445). The murine SM22α promoter can be isolated as described in Moessler et al. (1996, Development 122, 2415-2425). The SM22α promoter of the human gene is also suitable in the context of the present invention, particularly the portion extending approximately up to position −445 (i.e. positions 1 to 445 in SEQ ID NO: 14). The other mammalian forms of the SM22α promoter can be obtained using conventional molecular biology techniques or by PCR from an appropriate matrix (e.g a prior art plasmid as described in the precited literature). For example, fragments of the murine gene can be used to probe a genomic library made from other species of mammals under conditions allowing homologous sequences to hybridize. Appropriate hybridization conditions can be determined by reference to standard manuals (e.g. Sambrook et al., 1989, Molecular cloning, Cold Spring Harbor, N.Y.).

The term "muscle" as used herein is intended to designate any type of muscle cells, including skeletal, cardiac and smooth muscles (as defined above). Skeletal and smooth muscles are preferred in the context of the present invention.

A "muscle-specific enhancer" as used herein refers to a polynucleotide sequence to which (a) factor(s) bind(s) directly or indirectly (i.e. through interaction with another cellular factor), thereby enhancing gene expression driven by the SMC-specific promoter present in the chimeric construct of the invention, especially in the targeted SMCs. Such an enhancement can be determined by comparing for example the expression of a reporter gene under the control of the SMC-specific promoter in the presence or in the absence of the muscle-specific enhancer, either in vitro (e.g. in cultured SMCs) or in vivo (e.g. in transgenic animals or by direct administration to animal models) and under the same experimental conditions. Examples of such gene expression analysis is provided in Examples 3, 4 and 6 of the present specification, however other methods well known by those skilled in the art are also usable in the context of the invention.

A large number of muscle-specific enhancers from a variety of different sources are well known in the art and available as or within cloned polynucleotide sequences (from e.g. depositories such as ATCC or other commercial and individual sources). Accordingly, in a preferred embodiment, the muscle-specific enhancer is selected from the group of enhancers of the genes encoding:

a) a mammalian α-actin (Shimizu et al., 1995, J. Biol. Chem. 270, 7631-7643), especially the cardiac, the skeletal or the smooth muscle α-actin (Genbank accession number D00618);

b) a mammalian troponin, especially the troponin C (Genbank accession number M37984), I (Genbank accession number X90780) or T (Genbank accession number AJ011712);

c) a mammalian myogenin (Genbank accession number X62155);

d) a mammalian myosin. Several myosin enhancers have been identified to date from both myosin light chain and myosin heavy chain genes (for example Donoghue et al., 1988, Genes and Development 2, 1779-1790). Preferred is a myosin heavy chain enhancer, more preferred one of rabbit, with a special preference for the enhancer located between positions approximately −1332 and approximately −1225 (SEQ ID NO: 2) upstream of the transcription initiation site of the rabbit myosin heavy chain encoding gene (Kallmeier et al., 1995, J. Biol. Chem. 270, 30949-30957);

e) a mammalian creatine kinase, especially of human (Trask et al., 1988, J. Biol. Chem., 263, 17142-17149; Genbank accession number AH003460) or mouse (Jaynes et al., 1988, Mol. Cell. Biol. 8, 62-70). A preferred muscle-specific enhancer employs preferably the sequence located between positions approximately −919 and approximately −711 (SEQ ID NO: 3) upstream of the transcription initiation site of the human creatine kinase gene;

f) a mammalian APEG-1 (Aortic preferentially expressed gene-1; Hsieh et al., 1999, J. Biol. Chem. 274, 14344-14351);

g) a mammalian smoothelin (Genbank accession number AH007691);

h) a mammalian SM20 gene product, especially of human origin (Wax et al., 1996, Lab. (Invest. 74, 797-808);

i) a mammalian Timp4 (Tissue inhibitor of metalloproteinase 4), especially of human origin (Genbank accession number U76456);

j) a mammalian calponin, with a special preference for the sequence located between positions approximately +138 and approximately +1875 within the first intron of the murine calponin gene (Miano et al., 2000, J. Biol. Chem. 275, 9814-9822).

<<Operably linked>> refers to a juxtaposition of nucleic acid sequences (i) and (ii) wherein the muscle-specific enhancer and the SMC-specific promoter are in a relationship permitting them to function in their intended manner. The muscle-specific enhancer is operably linked to the SMC-specific promoter if the enhancer increases gene expression driven by the promoter. An operably linked enhancer can be placed in the chimeric construct upstream, downstream of the promoter or within the gene sequence and can be adjacent, at a close distance or over distances up to several kb. Advantageously, the muscle-specific enhancer is positioned upstream of the SMC-specific promoter with a distance separating the promoter and the enhancer being less than 500 bp, preferably less than 200 bp and, more preferably immediately upstream of the promoter. Moreover, the orientation of the muscle-specific enhancer may be sense (5'→3') or antisense (3'→5') relative to the transcriptional direction conferred by the SMC-specific promoter. In the context of the present invention, the chimeric construct comprises preferably the creatine kinase enhancer positioned in antisense orientation or the myosin heavy chain enhancer positioned in sense orientation relative to the SMC-specific promoter. The calponin enhancer is preferably inserted downstream of the SMC-specific promoter (i.e. as an intron or within an intron). Also encompassed are chimeric constructs which contain more than one muscle-specific enhancer as hereinabove defined.

The operability of the chimeric construct of the present invention may be easily determined by measuring its capability to drive gene expression (e.g. a reporter gene encoding for example the bacterial enzyme chloramphenicol acetyltransferase (CAT), β-galactosidase, luciferase or eGFP) in SMCs, either in vitro in appropriate cultured cells or in vivo (in transgenic animals or by direct administration to animal models). Gene expression can be determined by standard methods such as flow cytometry, ELISA, immunofluorescence, Western blotting, biological activity measurement and the like.

Moreover, the gene expression activity of the chimeric construct of the invention can be compared to strong promoters/enhancers, such as CMV which is considered as one of the most active known at present but which is non-specific (ubiquitous expression). The chimeric construct of the present invention provides expression levels of the reporter gene in SMCs of at least 10%, advantageously at least 15%, preferably at least 20% and more particularly between approximately 20 and 35% of that obtained with the CMV promoter/enhancer under comparable experimental conditions, especially when a murine SMC-specific promoter is used (e.g. the portion of the murine SM22α promoter from approximately −445 to approximately +65 relative to the cap site). The expression level can reach at least 15%, preferably between 20 to 200% of that obtained with the reference CMV promoter/enhancer when using a chimeric construct supplied with a human SMC-specific promoter (e.g. the portion of the human SM22α promoter from approximately 445 to approximately +63 relative to the cap site). In non-SMCs, the gene expression driven by the chimeric construct of the present invention is low (less than 5%, advantageously less than 2% and preferably less than 1% of that obtained with the CMV construct) or undetectable.

A chimeric construct may be constructed by standard molecular biology techniques well known in the art. The SMC-specific promoter and the muscle-specific enhancer can for example be isolated by cloning techniques from DNA libraries or by amplification methods (PCR) using appropriate probes. Alternatively, they may be produced by chemical synthesis based upon sequence data available in the art. The promoter- and enhancer-bearing fragments can be associated by means of using restriction enzymes and ligases to generate the chimeric construct of the invention.

In the context of the present invention, each of the promoter or enhancer or both can be modified by deletion, addition and/or substitution of one or several nucleotide(s), provided that their respective activity as defined above be substantially preserved (at least 80% of the activity of the native sequence). Such modifications can be aimed to remove (i) positive cis-acting sequences which control expression in cell types other than SMCs (improvement of SMC-specificity) or (ii) negative cis-acting sequences (<<silencer>>) which reduce expression levels. Site-directed mutagenesis can be used to modify the native sequence.

The present invention also relates to a SMC-specific promoter comprising a portion of the human SM22α promoter sufficient to drive gene expression essentially in a SMC lineage restricted fashion (visceral and/or vascular SMCs). The SMC specificity can be demonstrated by any conventional technique in the art, such as those described above using cultured cells, transgenic animals or in vivo administration. Preferably, the SMC-specific promoter of the invention comprises or, preferably consists in all or part of the sequence specified in SEQ ID NO: 14, more preferably extending from approximately nucleotide 1 to approximately nucleotide 445 (corresponding to approximately positions 445 to −1 of the human SM22α gene relative to the cap site) or any functional equivalent thereof (modified with respect to the native sequence by addition, deletion and/or substitution of one or more nucleotide(s) and preserving at least 80% of the activity of the native sequence in terms of SMC-specificity and/or expression levels).

The present invention also provides an expression cassette comprising a gene of interest placed under the control of a chimeric construct or a SMC-specific promoter according to the invention, allowing its expression in a target cell.

The term "gene of interest" refers to a nucleic acid which can be of any origin and isolated from a genomic DNA, a cDNA, or any DNA encoding a RNA, such as a genomic RNA, a mRNA, an antisense RNA, a ribosomal RNA, a ribozyme or a transfer RNA. The gene of interest can also be an oligonucleotide (i.e. a nucleic acid having a short size of less than 100 bp).

In a preferred embodiment, the gene of interest in use in the present invention, encodes a gene product of therapeutic interest. A "gene product of therapeutic interest" is one which has a therapeutic or protective activity when administered appropriately to a patient, especially a patient suffering from a disease or illness condition or who should be protected against this disease or condition. Such a therapeutic or protective activity can be correlated to a beneficial effect on the course of a symptom of said disease or said condition. It is within the reach of the man skilled in the art to select a gene encoding an appropriate gene product of therapeutic interest, depending on the disease or condition to be treated. In a general manner, his choice may be based on the results previously obtained, so that he can reasonably expect, without undue experimentation, i.e. other than practicing the invention as claimed, to obtain such therapeutic properties.

In the context of the invention, the gene of interest can be homologous or heterologous to the target cell into which it is introduced. Advantageously, it encodes a polypeptide, a ribozyme or an antisense RNA. The term <<polypeptide>> is to be understood as any translational product of a polynucleotide whatever its size is, and includes polypeptides having as few as 7 residues (peptides), but more typically proteins. In addition, it may be from any origin (prokaryotes, lower or higher eukaryotes, plant, virus etc). It may be a native polypeptide, a variant, a chimeric polypeptide having no counterpart in nature or fragments thereof. Advantageously, the gene of interest in use in the present invention encodes at least one polypeptide that can compensate for one or more defective or deficient cellular proteins in an animal or a human organism, or that acts through toxic effects to limit or remove harmful cells from the body. A suitable polypeptide may also be immunity conferring and acts as an antigen to provoke a humoral or a cellular response, or both.

Examples of polypeptides encoded by the gene of interest in use in the expression cassette of the present invention include without limitation polypeptides selected from the group consisting of:

polypeptides involved in the cellular cycle, such as p21, p16, the expression product of the restinoblastoma (Rb) gene, kinase inhibitors (preferably of the cyclin-dependent type), GAX, GAS-1, GAS-3, GAS-6, Gadd45 and cyclin A, B and D;

apoptosis inducers, such as p53, Bas, Bcl2, BclX, Bad and their antagonists;

angiogenic polypeptides, such as members of the family of vascular endothelial growth factors (VEGF), transforming growth factor (TGF, and especially TGF α and β), epithelial growth factors (EGF), fibroblast growth factor (FGF and especially FGF α and β), tumor necrosis factors (TNF, especially TNF α and β), CCN (including CTGF, Cyr61, Nov, Elm-1, Cop-1 and Wisp-3), scatter factor/hepatocyte growth factor (SH/HGF), angiogenin, angiopoïetin (especially 1 and 2), angiotensin-2, cytokines (including interleukins, in particular IL-2, IL-8, colony stimulating factors such as GM-CSF, G-CSF, M-C SF), plasminogen activator (tPA) and urokinase (uPA);

polypeptides capable of decreasing or inhibiting a cellular proliferation, including antibodies, toxins, immunotoxins, polypeptides inhibiting the oncogen expression products (e.g. ras, map kinase, tyrosine kinase receptors, growth factors), Fas ligand, suicide gene products;

polypeptides capable of modulating or regulating the expression of cellular genes;

coagulation factors (FVIII, FIX . . . );

immunostimulatory polypeptides such as B7.1, B7.2, ICAM and the like;

enzymes, such as urease, renin, thrombin, metalloproteinase, nitric oxide synthases eNOS or iNOS, SOD, catalase, heme oxygenase, the lipoprotein lipase family;

oxygen radical scavengers;

enzyme inhibitors, such as alpha1-antitrypsin, antithrombin III, plasminogen activator inhibitor PAI-1, tissue inhibitor of metalloproteinase 1-4 dystrophin;

angiogenesis inhibitors, such as angiostatin, endostatin, platelet factor-4, cytokines such as IL-12, IFNβ or γ;

transcription factors, such as nuclear receptors comprising a DNA binding domain, a ligand binding domain and domain activating or inhibiting transcription (e.g. fusion products derived from oestrogen, steroid and progesterone receptors);

markers (β-galactosidase, CAT, luciferase, GFP . . . ); and any polypeptides that are recognized in the art as being useful for the treatment or prevention of a clinical condition.

It is within the scope of the present invention that the gene of interest may include addition(s), deletion(s) and/or modification(s) of one or more nucleotide(s) with respect to the native sequence.

In the context of the invention, a suicide gene product is capable of converting an inactive substance prodrug) into a cytotoxic substance, thereby giving rise to cell death. The gene encoding the thymidine kinase (TK) of HSV-1 constitutes the prototype of the suicide gene family (Caruso et al., 1993, Proc. Natl. Acad. Sci. USA 90, 7024-7028; Culver et al., 1992, Science 256, 1550-1552), and catalyzes the transformation of nucleoside analogs (prodrug) such as acyclovir or ganciclovir to toxic nucleosides that are incorporated into the neoformed DNA chains, leading to inhibition of cell division. A large number of suicide gene/prodrug combinations are currently available. Those which may more specifically be mentioned are the bacterial and fungal genes encoding cytosine deaminase (Erbs et al., 1997, Curr. Genet. 31, 1-6; WO93/01281; EP 402 108) and uracil phosphoribosyl transferase (Anderson et al., 1992, Eur. J. Biochem. 204, 51-56;

Kern et al., 1990, Gene 88, 149-157), which can be used with the prodrug 5-fluorocytosine (5-FC). The present invention also encompasses the use of mutant suicide genes, such as those described in WO96/16183 and WO99/54481.

Another preferred embodiment relates to expression cassettes, wherein the gene of interest encodes a polypeptide having growth suppressive activities on SMCs. Accordingly, in a further preferred embodiment, the polypeptide is selected from the group consisting of IFN β (Genbank accession number M25460), IFNγ (Genbank accession number M29383), nitric oxide synthase eNOS (Genbank accession number M95296), Fas ligand (Genbank accession number U08137), heme oxygenase (Genbank accession number X06985), interleukin-10 (Genbank accession number U16720) and heparin-binding VEGF (Genbank accession number M32977), preferably each of human origin.

As mentioned above, the gene of interest also includes genes encoding antisense sequences and ribozymes capable of binding and inactivating specific cellular RNA, preferably that of selected positively-acting growth regulatory genes, such as oncogenes and protooncogenes (c-myc, c-fos, c-jun, c-myb, c-ras, Kc and JE).

The expression cassette of the present invention may comprise one or more gene(s) of interest. In this regard, the combination of genes encoding a suicide gene product and a cytokine (such as IL-2, IL-8, IFNγ, GM-CSF) or an immunostimulatory polypeptide (such as B7.1, B7.2, ICAM and the like) may be advantageous in the context of the invention. The different genes of interest may be controlled by the chimeric construct or the SMC-specific promoter of the invention (polycistronic cassette) or by independent promoters, at least one being the chimeric construct or the SMC-specific promoter defined above, that are positioned either in the same or in opposite directions. Furthermore, they may be carried by the same vector or by independent vectors.

The expression construct of the present invention may further comprise additional functional elements, such as exon/intron sequences, targeting sequences, transport sequences, secretion signal sequences, nuclear localization signal sequences, IRES, polyA transcription termination sequences, tripartite leader sequences, sequences involved in replication or integration. Said sequences have been reported in the literature and can be readily obtained by those skilled in the art.

In a preferred embodiment, the expression cassette of the invention further comprises one or more exon(s) or (a) portion(s) thereof, preferably, non-coding exon(s), and optionally, one or more intron(s). Such exon and/or intron sequences may be advantageous for stabilizing expression and may for example be obtained from the gene from which the SMC-specific promoter originates (e.g. SM22α) or from any other origin (e.g. eukaryotic, viral, synthetic). The large variety of exon/intron sequences described in the state of the art are suitable in the context of the present invention. They are preferably inserted after the transcription initiation site and before the gene of interest.

Referring to the preferred embodiment of the chimeric construct that comprises the mouse SM22α promoter, an appropriate exon sequence comprises the portion of the first non-coding exon extending from position +1 to approximately position +65 of the mouse SM22α gene (i.e. in SEQ ID NO: 1 from positions 446 to 510) or from position +1 to approximately position +63 of the human SM22α gene (i.e. in SEQ ID NO: 14 from positions 446 to 508).

The expression cassette of the present invention may also contain a polyadenylation signal operably linked to the gene(s) of interest. A polyadenylation sequence is operably linked to the gene to be transcribed, when it allows termination of the transcription. It is preferably positioned 3' (downstream) of the gene of interest.

The present invention also provides a vector comprising an expression cassette according to the invention. The skilled person may choose the appropriate vector out of a wide range of vectors. For instance, the vector may be a naked DNA molecule, for instance in the form of a plasmid or a viral vector, eventually complexed or mixed to (a) synthetic vector(s). The term "plasmid" denotes an extrachromosomal circular DNA capable of autonomous replication in a given cell. The range of suitable plasmids is very large. Preferably, the plasmid is designed for amplification in bacteria and for expression in an eukaryotic target cell. Such plasmids can be purchased from a variety of manufacturers. Suitable plasmids include but are not limited to those derived from pBR322 (Gibco BRL), pUC (Gibco BRL), pBluescript (Stratagene), pREP4, pCEP4 (Invitrogene), pCI (Promega) and p Poly (Lathe et al., Gene 57 (1987), 193-201). It can also be engineered by standard molecular biology techniques (Sambrook et al., Laboratory Manual, Cold Spring Harbor Laboratory Press, Cold Spring Harbor (1989), NY). It may also comprise a selection gene in order to select or to identify the transfected cells (e.g. by complementation of a cell auxotrophy or by antibiotic resistance), stabilizing elements (e.g. cer sequence; Summers and Sherrat, Cell 36 (1984), 1097-1103) or integrative elements (e.g. LTR viral sequences and transposons).

A preferred embodiment of the vectors of the invention relates to viral vectors derived from a virus selected from the group consisting of herpes viruses, cytomegaloviruses, foamy viruses, lentiviruses, Semliki forrest virus, AAV (adeno-associated virus), poxviruses, adenoviruses and retroviruses. Such viral vectors are well known in the art. <<Derived>> means genetically engineered from the native viral genome by introducing one or more modifications, such as deletion(s), addition(s) and/or substitution(s) of one or several nucleotide(s) present in a coding or a non-coding portion of the viral genome.

A viral vector which is particularly appropriate for the present invention is an adenoviral vector. The adenoviral genome consists of a linear double-standed DNA molecule of approximately 36 kb carrying more than about thirty genes necessary to complete the viral cycle. The early genes are divided into 4 regions (E1 to E4) that are essential for viral replication with the exception of the E3 region, which is believed to modulate the anti-viral host immune response. The E1 region (E1A and E1B) encodes proteins responsible for the regulation of transcription of the viral genome. Expression of the E2 region genes (E2A and E2B) leads to the synthesis of the polypeptides needed for viral replication (Pettersson and Roberts, 1986, In Cancer Cells (Vol 4): DNA Tumor Viruses, Botchan and Glodzicker Sharp Eds pp 37-47, Cold Spring Harbor Laboratory, Cold Spring Harbor, N.Y.). The proteins encoded by the E3 region prevent cytolysis by cytotoxic T cells and tumor necrosis factor (Wold and Gooding, 1991, Virology 184, 1-8). The proteins encoded by the E4 region are involved in DNA replication, late gene expression and splicing and host cell shut off (Halbert et al., 1985, J. Virol. 56, 250-257). The late genes encode in their majority the structural proteins constituting the viral capsid. In addition, the adenoviral genome carries at both extremities cis-acting 5' and 3' ITRs (Inverted Terminal Repeat) and packaging sequences essential for DNA replication. The ITRs harbor origins of DNA replication whereas the encapsidation region is required for the packaging of adenoviral DNA into infectious particles.

In one embodiment, the adenoviral vector of the present invention is engineered to be conditionally replicative (CRAd vectors) in order to replicate selectively in specific cells (e.g. proliferative cells) as described in Heise and Kim (2000, J. Clin. Invest. 105, 847-851).

According to another and preferred embodiment, the adenoviral vector of the invention is replication-defective, at least for the E1 function by total or partial deletion and/or mutation of one or more genes constituting the E1 region. Advantageously, the E1 deletion covers nucleotides (nt) 458 to 3328 or 458 to 3510 by reference to the sequence of the human adenovirus type 5 disclosed in the Genebank data base under the accession number M 73260.

Furthermore, the adenoviral backbone of the vector may comprise additional modifications (deletions, insertions or mutations in one or more viral genes). An example of an E2 modification is illustrated by the thermosensible mutation localized on the DBP (DNA Binding Protein) encoding gene (Ensinger et al., 1972, J. Virol. 10, 328-339). The adenoviral sequence may also be deleted of all or part of the E4 region. A partial deletion retaining the ORFs 3 and 4 or ORFs 3 and 6/7 may be advantageous (see for example European application EP 974 668; Christ et al., 2000, Human Gene Ther. 11, 415-427; Lusky et al., 1999, J. Virol. 73, 8308-8319). Additional deletions within the non-essential E3 region may increase the cloning capacity (for a review see for example Yeh et al. FASEB Journal 11 (1997) 615-623), but it may be advantageous to retain all or part of the E3 sequences coding for the polypeptides (e.g. gp19k) allowing to escape the host immune system (Gooding et al., 1990, Critical Review of Immunology 10, 53-71) or inflammatory reactions (EP00440267.3). Second generation vectors retaining the ITRs and packaging sequences and containing substantial genetic modifications aimed to abolish the residual synthesis of the viral antigens may also be envisaged, in order to improve long-term expression of the expressed gene in the transduced cells (WO94/28152; Lusky et al., 1998, J. Virol 72, 2022-2032).

The expression cassette of the present invention can be inserted in any location of the adenoviral genome, with the exception of the cis-acting sequences. Preferably, it is inserted in replacement of a deleted region (E1, E3 and/or E4), with a special preference for the deleted E1 region. In addition, the expression cassette may be positioned in sense or antisense orientation relative to the transcriptional direction of the region in question.

Adenoviruses adaptable for use in accordance with the present invention, can be derived from any human or animal source, in particular canine (e.g. CAV-1 or CAV-2; Genbank ref CAV1GENOM and CAV77082 respectively), avian (Genbank ref AAVEDSDNA), bovine (such as BAV3; Seshidhar Reddy et al., 1998, J. Virol. 72, 1394-1402), murine (Genbank ref ADRMUSMAV1), ovine, feline, porcine or simian adenovirus or alternatively from a hybrid thereof. Any serotype can be employed. However, the human adenoviruses of the C sub-group are preferred and especially adenoviruses 2 (Ad2) and 5 (Ad5). Generally speaking, the cited viruses are available in collections such as ATCC and have been the subject of numerous publications describing their sequence, organization and biology, allowing the artisan to apply them.

In addition, adenoviral particles or empty adenoviral capsids can also be used to transfer nucleic acids (e.g. a plasmidic vector) by a virus-mediated cointernalization process as described in U.S. Pat. No. 5,928,944. This process can be accomplished in the presence of (a) cationic agent(s) such as polycarbenes or lipid vesicles comprising one or more lipid layers.

A retroviral vector is also suitable. Retroviruses are a class of integrative viruses which replicate using a virus-encoded reverse transcriptase, to replicate the viral RNA genome into double stranded DNA which is integrated into chromosomal DNA of the infected cells. The numerous vectors described in the literature may be used within the framework of the present invention and especially those derived from murine leukemia viruses, especially Moloney (Gilboa et al., 1988, Adv. Exp. Med. Biol. 241, 29) or Friend's FB29 strains (WO95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (U.S. Pat. No. 5,747,323). The expression cassette of the invention is inserted downstream of the encapsidation sequence, preferably in opposite direction relative to the retroviral genome.

Poxviruses are a group of complex enveloped viruses that distinguish from the above-mentioned viruses by their large DNA genome and their cytoplasmic site of replication. The genome of several members of poxviridae has been mapped and sequenced. It is a double-stranded DNA of approximately 200 kb coding for about 200 proteins of which approximately 100 are involved in virus assembly. In the context of the present invention, a poxviral vector may be obtained from any member of the poxviridae, in particular canarypox, fowlpox and vaccinia virus, the latter being preferred. Suitable vaccinia viruses include without limitation the Copenhagen strain (Goebel et al., 1990, Virol. 179, 247-266 and 517-563; Johnson et al., 1993, Virol. 196, 381-401), the Wyeth strain and the modified Ankara (MVA) strain (Antoine et al., 1998, Virol. 244, 365-396). The general conditions for constructing a vaccinia virus comprising an expression cassette according to the present invention are well known in the art (see for example EP 83 286 and EP 206 920 for Copenhagen vaccinia viruses and Mayr et al., 1975, Infection 3, 6-14 and Sutter and Moss, 1992, Proc. Natl. Acad. Sci. USA 89, 10847-10851 for MVA viruses).

The expression cassette of the present invention is preferably inserted within the poxviral genome in a non-essential locus, such as non-coding intergenic regions or any gene for which inactivation or deletion does not significantly impair viral growth and replication. Thymidine kinase gene is particularly appropriate for insertion in Copenhagen vaccinia viruses (Hruby et al., 1983, Proc. Natl. Acad. Sci. USA 80, 3411-3415; Weir et al., 1983, J. Virol. 46, 530-537). As far as MVA is concerned, insertion of the expression cassette can be performed in any of the excisions I to VII, and preferably in excision II or III (Meyer et al., 1991, J. Gen. Virol. 72, 1031-1038; Sutter et al., 1994, Vaccine 12, 1032-1040) or in D4R locus. For fowlpox virus, although insertion within thymidine kinase gene may be considered, the expression cassette is preferably introduced into a non-coding intergenic region (see for (example EP 314 569 and U.S. Pat. No. 5,180,675). One may also envisage insertion in an essential viral locus provided that the defective function be supplied in trans, via a helper virus or by expression in the producer cell line.

According to an advantageous alternative, a vector of the present invention may be complexed to lipids and/or polymers (synthetic vector). Preferred lipids are cationic lipids which have a high affinity for nucleic acids and which interact with cell membranes (Felgner et al. Nature 337 (1989) 387-388). As a result, they are capable of complexing the nucleic acid, thus generating a compact particle capable of entering the cells. Suitable lipids include without limitation DOTMA (Felgner et al., Proc. Natl. Acad. Sci. USA 84 (1987), 7413-7417), DOGS or Transfectam™ (Behr et al., Proc. Natl. Acad. Sci. USA 86 (1989), 6982-6986), DMRIE or DORIE (Felgner et al., Methods 5 (1993), 67-75), DC-CHOL (Gao and Huang, BBRC 179 (1991), 280-285), DOTAP™ (McLachlan et al., Gene Therapy 2 (1995), 674-622), Lipofectamine™ and glycerolipid compounds (see EP901463 and WO98/37916).

Suitable polymers are preferably cationic, such as polyamidoamine (Haensler and Szoka, Bioconjugate Chem. 4 (1993), 372-379), dendritic polymer (WO 95/24221), polyethylene imine or polypropylene imine (WO 96/02655), polylysine (U.S. Pat. No. 5,595,897 or FR 2 719 316), chitosan (U.S. Pat. No. 5,744,166) or DEAE dextran (Lopata et al. Nucleic Acid Res. 12 (1984) 5707-5717).

In a further embodiment, the present invention relates to a method for the preparation of viral particles allowing the SMC-specific expression of a gene of interest in a target cell, said method comprising the steps of:

a) introducing a viral vector of the invention in a permissive cell line;
b) culturing the permissive cell line obtained in step a) for an appropriate period of time and under suitable conditions to allow the production of said viral particles;
c) recovering said viral particles from the cell culture; and
d) optionally, purifying the recovered viral particles.

In a preferred embodiment, the permissive cell line is a complementation cell line which provides in trans all gene products necessary to produce infectious virions.

The present invention also provides viral particles comprising a vector according to the invention, preferably a viral vector, or obtainable by the method for the preparation of such viral particles.

Adenoviral particles may be prepared and propagated according to any conventional technique in the field of the art (e.g. as described in Graham and Prevect, 1991, Methods in Molecular Biology, Vol 7, Gene Transfer and Expression Protocols; Ed E. J. Murray, The Human Press Inc, Clinton, N.J. or in WO96/17070) using a complementation cell line or a helper virus, which supplies in trans the viral genes for which the adenoviral vector of the invention is defective. The cell lines 293 (Graham et al., 1977, J. Gen. Virol. 36, 59-72) and PERC6 (Fallaux et al., 1998, Human Gene Therapy 9, 1909-1917) are commonly used to complement the E1 function. Other cell lines have been engineered to complement doubly defective vectors (Yeh et al., 1996, J. Virol. 70, 559-565; Krougliak and Graham, 1995, Human Gene Ther. 6, 1575-1586; Wang et al., 1995, Gene Ther. 2, 775-783; Lusky et al., 1998, J. Virol. 72, 2022-2033; EP919627 and WO97/04119). The adenoviral particles can be recovered from the culture supernatant but also from the cells after lysis and optionally further purified according to standard techniques (e.g. chromatography, ultracentrifugation, as described in WO96/27677, WO98/00524 WO98/26048 and WO00/50573).

Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7, 980; Danos and Mulligan, 1988, Proc. Natl. Acad. Sci. USA 85, 6460; Markowitz et al., 1988, Virol. 167, 400). The product of the env gene is responsible for the binding of the viral particle to the viral receptors present on the surface of the target cell and, therefore determines the host range of the retroviral particle. In the context of the invention, it is advantageous to use a packaging cell line, such as the PA317 cells (ATCC CRL 9078) or 293E16 (WO97/35996) containing an amphotropic envelope protein, to allow infection of human and other species' target cells. The retroviral particles are preferably recovered from the culture supernatant and may optionally be further purified according to standard techniques (e.g. chromatography, ultracentrifugation).

Poxviral particles are prepared as described in numerous documents accessible to the artisan skilled in the art (Piccini et al., 1987, Methods of Enzymology 153, 545-563; U.S. Pat. No. 4,769,330; U.S. Pat. No. 4,772,848; U.S. Pat. No. 4,603,112; U.S. Pat. No. 5,100,587 and U.S. Pat. No. 5,179,993). The major techniques that have been developed utilize homologous recombination between a donor plasmid containing the expression cassette of the invention flanked on both sides by pox DNA sequences (encompassing the desired insertion site) and the wild type poxviral genome. Generally, the donor plasmid is constructed, amplified by growth in *E. coli* and isolated by conventional procedures. Then, it is introduced into a suitable cell culture (e.g. chicken embryo fibroblasts) together with a poxvirus genome, to produce by homologous recombination the poxviral particles of the invention. They can be recovered from the culture supernatant or from the cultured cells after a lysis step (chemical, freezing/thawing, osmotic shock, mechanic shock, sonication and the like) and can be, if necessary, isolated from wild type contamination by consecutive rounds of plaque purification and then purified using the techniques of the art (chromatographic methods, ultracentrifugation on cesium chloride or sucrose gradient).

The present invention also encompasses vectors or particles that have been modified to allow preferential targeting of a particular target cell. A characteristic feature of targeted vectors/particles of the invention (of both viral and non-viral origins, such as polymer- and lipid-complexed vectors) is the presence at their surface of a targeting moiety capable of recognizing and binding to a cellular and surface-exposed component or to the extracellular matrix (ECM) such as collagen; Hall et al., 2000, Human Gene Therapy 11, 983-993). Such targeting moieties include without limitation chemical conjugates, lipids, glycolipids, hormones, sugars, polymers (e.g. PEG, polylysine, PEI and the like), peptides, polypeptides (for example JTS1 as described in WO 94/40958), oligonucleotides, vitamins, antigens, lectins, antibodies and fragments thereof. They are preferably capable of recognizing and binding to cell-specific markers, tissue-specific markers, cellular receptors, viral antigens, antigenic epitopes or tumor-associated markers.

Cell type-specific targeting may be achieved with vectors derived from viruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment (Defer et al. J. Virol. 64 (1990) 3661-3673). Thus, cell targeting of adenoviruses can be carried out by genetic modification of the viral gene encoding fiber and/or penton, to generate modified fiber and/or penton capable of specific interaction with unique cell surface receptors. Examples of such modifications are described in literature (for example in Wickam et al., 1997, J. Virol. 71, 8221-8229; Amberg et al., 1997, Virol. 227, 239-244; Michael et al., 1995, Gene Therapy 2, 660-668; WO94/10323). To illustrate, inserting a sequence coding for EGF within the sequence encoding the adenoviral fiber will allow to target EGF receptor expressing cells Other methods for cell specific targeting have been achieved by the conjugation of antibodies or antibody fragments to the retroviral envelope protein (Michael et al., 1993, J. Biol. Chem 268, 6866-6869; Roux et al., 1989, Proc. Natl. Acad Sci. USA 86, 9079-9083; Miller and Vile, 1995, FASEB J. 9, 190-199 and WO93/09221) and of polypeptides having a nucleic acid binding domain and a targeting moiety (WO95/28494).

The present invention also provides an eukaryotic host cell comprising an expression cassette or a vector according to the invention or infected by a viral particle according to the invention. In the context of the present invention, the term "eukaryotic host cell" designates any cell comprising one or several transcriptional factors capable of interacting with the cis-acting sequences present in the SMC-specific promoter and/or the muscle-specific enhancer in use in the present invention. Such cells may be unique type of cells or a group of different types of cells and encompass cultured cell lines, primary cells and proliferative cells from mammalian origin, with a special preference for human origin. Preferred eukaryotic host cells include fibroblasts and muscle cells (such as cardiomyocytes, myofibroblasts and SMCs) and, especially, vascular SMCs. Among the latters, arterial SMCs are absolute preference and especially from medial and neointimal SMCs.

The present invention also provides a pharmaceutical composition comprising an expression cassette, a vector, a viral particle or an eukaryotic host cell according to the present invention and, optionally, a pharmaceutically acceptable carrier. In a special case, the composition may comprise two or more expression cassettes, vectors, viral particles or eukaryotic host cells, which may differ by the nature (i) of the muscle-specific enhancer and/or (ii) of the SMC-specific promoter and/or (iii) of the therapeutic gene and/or (iv) of the vector backbone.

The composition according to the invention may be manufactured in a conventional manner for a variety of modes of administration including systemic, topical and localized administration. For systemic administration, injection is preferred, e.g. subcutaneous, intravenous, intraperitoneal, intrathecal, intracardiac (such as transendocardial and pericardial), intramuscular, intratumoral, intrapulmonary, intratracheal, intracoronary or intracerebroventricular and more especially intravascular or intraarterial. The administration may take place in a single dose or a dose repeated one or several times after a certain time interval. The appropriate administration route and dosage may vary in accordance with various parameters, as for example, the condition or disease to be treated, the stage to which it has progressed, the need for prevention or therapy and the therapeutic gene to be transferred. As an indication, a composition based on viral particles may be formulated in the form of doses of between $10^6$ and $10^{14}$ iu (infectious units), advantageously between $10^5$ and $10^{13}$ iu and preferably between $10^6$ and $10^{12}$ iu. The titer may be determined by conventional techniques. The doses of DNA vector are preferably comprised between 0.01 and 10 mg/kg, more especially between 0.1 and 2 mg/kg. The composition of the invention can be in various forms, e.g. in solid (e.g. powder, lyophilized form), liquid (e.g. aqueous).

In a preferred embodiment, the composition comprises a pharmaceutically acceptable carrier, allowing its use in a method for the therapeutic treatment of humans or animals. In this particular case, the carrier is preferably a pharmaceutically suitable injectable carrier or diluent which is non-toxic to a human or animal organism at the dosage and concentration employed (for examples, see Remington's Pharmaceutical Sciences, $16^{th}$ ed. 1980, Mack Publishing Co). It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g. Tris-HCl, acetate, phosphate), emulsifiers, solubilizers or adjuvants. The pH of the pharmaceutical preparation is suitably adjusted and buffered in order to be appropriate for use in humans or animals. Representative examples of carriers or diluents for an injectable composition include water, isotonic saline solutions which are preferably buffered at a physiological pH (such as phosphate buffered saline, Tris buffered saline, mannitol, dextrose, glycerol containing or not polypeptides or proteins such as human serum albumin). For example, such a composition may comprise 10 mg/ml mannitol, 1 mg/ml HSA, 20 mM Tris pH 7.2 and 150 mM NaCl.

In addition, the composition according to the present invention may include one or more stabilizing substance(s), such as lipids (e.g. cationic lipids, liposomes, lipids as described in WO98/44143), nuclease inhibitors, hydrogel, hyaluronidase (WO98/53853), collagenase, polymers, chelating agents (EP890362), in order to preserve its degradation within the animal/human body and/or improve transfection/infection of the vector into the host cell. Such substances may be used alone or in combination (e.g. cationic and neutral lipids). It may also comprise substances susceptible to facilitate gene transfer in arterial cells, such as a gel complex of poly-lysine and lactose (Midoux et al., 1993, Nucleic Acid Res. 21, 871-878) or poloxamer 407 (Pastore, 1994, Circulation 90, I-517). It has also been shown that adenovirus proteins are capable of destabilizing endosomes and enhancing the uptake of DNA into cells. The mixture of adenoviruses to solutions containing a lipid-complexed DNA vector or the binding of DNA to polylysine covalently attached to adenoviruses using protein cross-linking agents may substantially improve the uptake and expression of the recombinant gene (Curiel et al., 1992, Am. J. Respir. Cell. Mol. Biol. 6, 247-252).

The composition of the present invention is particularly intended for the preventive or curative treatment of disorders, conditions or diseases associated with blood vessels (preferably arteries) and/or the cardiovascular system, including without limitation hypertension, atherogenesis, intimal hyperplasia, (re)restenosis following angioplasty or stent placement, ischemia, neoplastic diseases (e.g. tumors and tumor metastasis), benign tumors, connective tissue disorders (e.g. rheumatoid arthritis, atherosclerosis), ocular angiogenic diseases (e.g. diabetic retinopathy, macular degeneration, corneal graft rejection, neovascular glaucoma), cardiovascular diseases, cerebral vascular diseases, diabetes-associated diseases and immune disorders (e.g. chronic inflammation or autoimmunity).

A preferred application is the prevention or treatment of ischemic heart diseases (acute or chronic). Balloon angioplasty is a major treatment which involves the inflation of a balloon in an occluded blood vessel in order to open the blocked blood vessel. Stent placement is also used to restore blood flow. Unfortunately, these methods of treatment frequently result in injury of the endothelial cells lining the inner wall of blood vessels. SMCs often infiltrate into the reopened blood vessels causing a secondary obstruction (a process called restenosis). Virus-mediated gene therapy may be applicable in this case to deliver to the lesion created by the balloon angioplasty or the stenting procedure, a therapeutic gene encoding a product inhibiting SMC proliferation.

The present invention also provides the use of an expression cassette, a vector, a viral particle or an eukaryotic host cell according to the invention, for the preparation of a drug for the treatment or the prevention of a disease in a human or animal organism by gene therapy.

Within the scope of the present invention, "gene therapy" has to be understood as a method for introducing any expressible sequence into a cell. Thus, it also includes immunotherapy that relates to the introduction of a potentially antigenic epitope into a cell to induce an immune response which can be cellular or humoral or both.

In a preferred embodiment, such a use is for the treatment or the prevention of a cardiovascular disease. For this purpose, the expression cassette, the vector or the viral particle of the present invention may be delivered in vivo to the human or animal organism by specific delivery means adapted to this pathology, such as catheters, stents and the like. For example, a balloon catheter or a stent coated with the expression cassette, vector or viral particle of the invention may be employed (as described in Riessen et al., 1993, Hum Gene Ther. 4, 749-758; Feldman and Steg, 1996, Medecine/Science 12, 47-55). The catheters suitable for use in the context of the present invention are available from commercial suppliers, such as Advanced Cardiovascular Systems (ACS), Boston Scientific, IVT, Target Therapeutics or Cordis or described in FR 00 08751. By way of illustration, a catheter can be conveniently introduced into a femoral artery and threaded retrograde through the iliac artery and abdominal aorta and into a coronary artery. Detailed descriptions of these techniques can be found in the art (e.g. Rutherford, Vascular Surgery, $3^{rd}$ edition (Saunders Co 1989). It is also possible to deliver the expression cassette, the vector or viral particle of the present invention directly to the arteries following surgical operation. Another alternative is to introduce along the affected artery a grid frame impregnated with the therapeutic agent (Feldman et al., 1995, J. Clin. Invest. 95, 2662-2671).

Alternatively, one may employ eukaryotic host cells that have been engineered ex vivo to contain an expression cassette, a vector or a viral particle according to the invention. Methods for introducing such elements into an eukaryotic cell are well known to those skilled in the art and include microinjection of minute amounts of DNA into the nucleus of a cell (Capechi et al., 1980, Cell 22, 479-488), transfection with $CaPO_4$ (Chen and Okayama, 1987, Mol. Cell Biol. 7, 2745-2752), electroporation (Chu et al., 1987, Nucleic Acid Res. 15, 1311-1326), lipofection/liposome fusion (Felgner et al., 1987, Proc. Natl. Acad. Sci. USA 84, 7413-7417) and particle bombardment (Yang et al., 1990, Proc. Natl. Acad. Sci. USA 87, 9568-9572). The graft of engineered SMCs is also possible in the context of the present invention (Lynch et al, 1992, Proc. Natl. Acad. Sci. USA 89, 1138-1142).

The present invention also relates to a method for the treatment of a human or animal organism, comprising administering to said organism a therapeutically effective amount of an expression cassette, a vector, a viral particle or an eukaryotic cell according to the invention.

A <<therapeutically effective amount>> is a dose sufficient for the alleviation of one or more symptoms normally associated with the disease or condition desired to be treated. When prophylactic use is concerned, this term means a dose sufficient to prevent or to delay the establishment of a disease or condition.

The method of the present invention can be used for preventive purposes and for therapeutic applications relative to the diseases or conditions listed above. The present method is particularly useful to prevent the establishment of restenosis or to reverse restenosis following angioplasty or stent placement procedures, using an approach similar to that described herein. It is to be understood that the present method can be carried out by any of a variety of approaches. Advantageously, the expression cassette, the vector or the pharmaceutical composition of the invention can be administered directly in vivo by any conventional and physiologically acceptable administration route, for example by intraarterial injection or by means of an appropriate catheter into the vascular system, etc. Alternatively, the ex vivo approach may also be adopted which consists of introducing an expression cassette, a vector or a viral particle according to the invention into cells, growing the transfected/infected cells in vitro and then reintroducing them into the patient to be treated.

In order to improve the transfection rate, the patient may undergo a macrophage depletion treatment prior to administration of the composition of the invention. Such a technique is described in literature (for example in Van Rooijen et al., 1997, TibTech, 15, 178-184).

When the method of the invention uses a pharmaceutical composition comprising an expression cassette expressing a suicide gene, it can be advantageous to additionally administer a pharmaceutically acceptable quantity of a prodrug which is specific for the expressed suicide gene product. The two administrations can be made simultaneously or consecutively, but preferably the prodrug is administered after the composition of the invention. By way of illustration, it is possible to use a dose of prodrug from 50 to 500 mg/kg/day, a dose of 200 mg/kg/day being preferred. The prodrug is administered in accordance with standard practice. The oral route is preferred. It is possible to administer a single dose of prodrug or doses which are repeated for a time sufficiently long to enable the toxic metabolite to be produced within the host organism or the target cell. As mentioned above, the prodrug ganciclovir or acyclovir can be used in combination with the TK HSV-1 gene product and 5-FC in combination with the cytosine deaminase and/or uracil phosphotransferase gene product.

Prevention or treatment of a disease or a condition can be carried out using the present method alone or, if desired, in conjunction with presently available methods (e.g. radiation, chemotherapy and surgery such as angioplasty).

The present invention also provides the use of the chimeric construct, the SMC-specific promoter, the expression cassette, the vector or the viral particle according to the invention, for specific expression in SMCs, and preferably in arterial SMCs, especially from media and/or neointima.

The present invention also provides a non-human transgenic animal, especially a transgenic mouse, comprising integrated into its genome an expression cassette or a vector according to the invention. Such an animal can be generated by conventional transgenesis methods and can be used as a model to study the potential effect or activity of the therapeutic gene or the regulation of the SMC-specific promoter and/or the muscle-specific enhancer present in the expression cassette of the invention.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

FIGURES LEGENDS

FIG. 1 illustrates the SM22α promoter strength in SMCs (Rat Ao, Rat IT15, Pig Co and Pig IT15) and A 549 cells. Results are presented as the percentage of the CMV global fluorescence index. Each cell type was exposed to either AdSM22eGFP or AdCMVeGFP at a MOI corresponding to the optimal infection. The global fluorescence index was determined by flow cytometry at D3.

Figure 2:
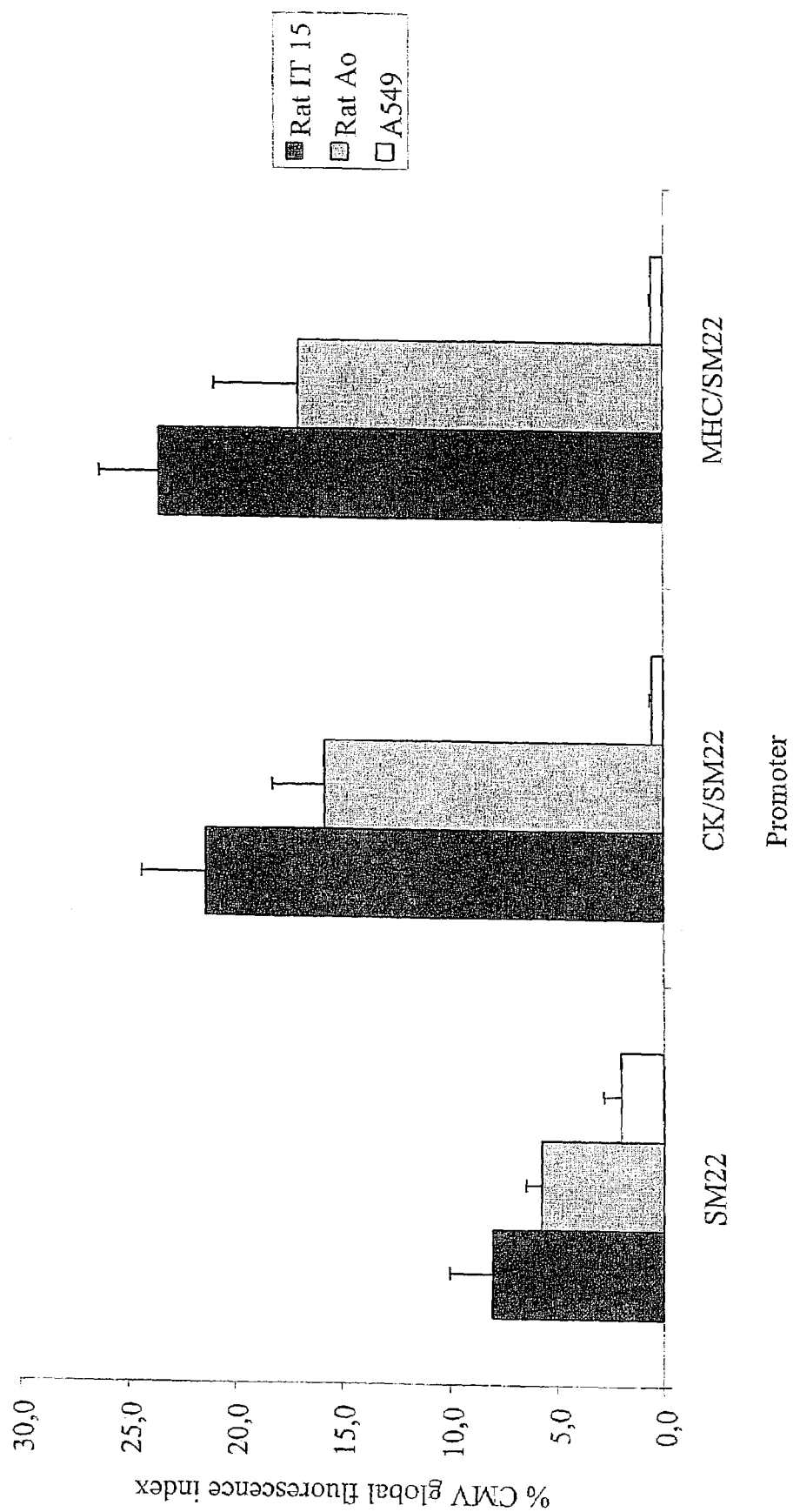

FIG. 2 illustrates the comparison of the vectors containing the murine SM22α promoter in SM versus non-SM cells. The SM22α promoter was used alone or in connection with the human creatine kinase enhancer (CK) or the rabbit SM-myosin heavy chain enhancer (MHC). Expression was analysed in rat IT15 (black bars), rat Ao (grey bars) and A549 (white bars). Results are presented as the percentage of the CMV global fluorescence index. Each cell type was exposed to SM22α promoter containing vectors and AdCMVeGFP at the appropriate MOI. The global fluorescence index was determined by flow cytometry at D3.

Figure 3:
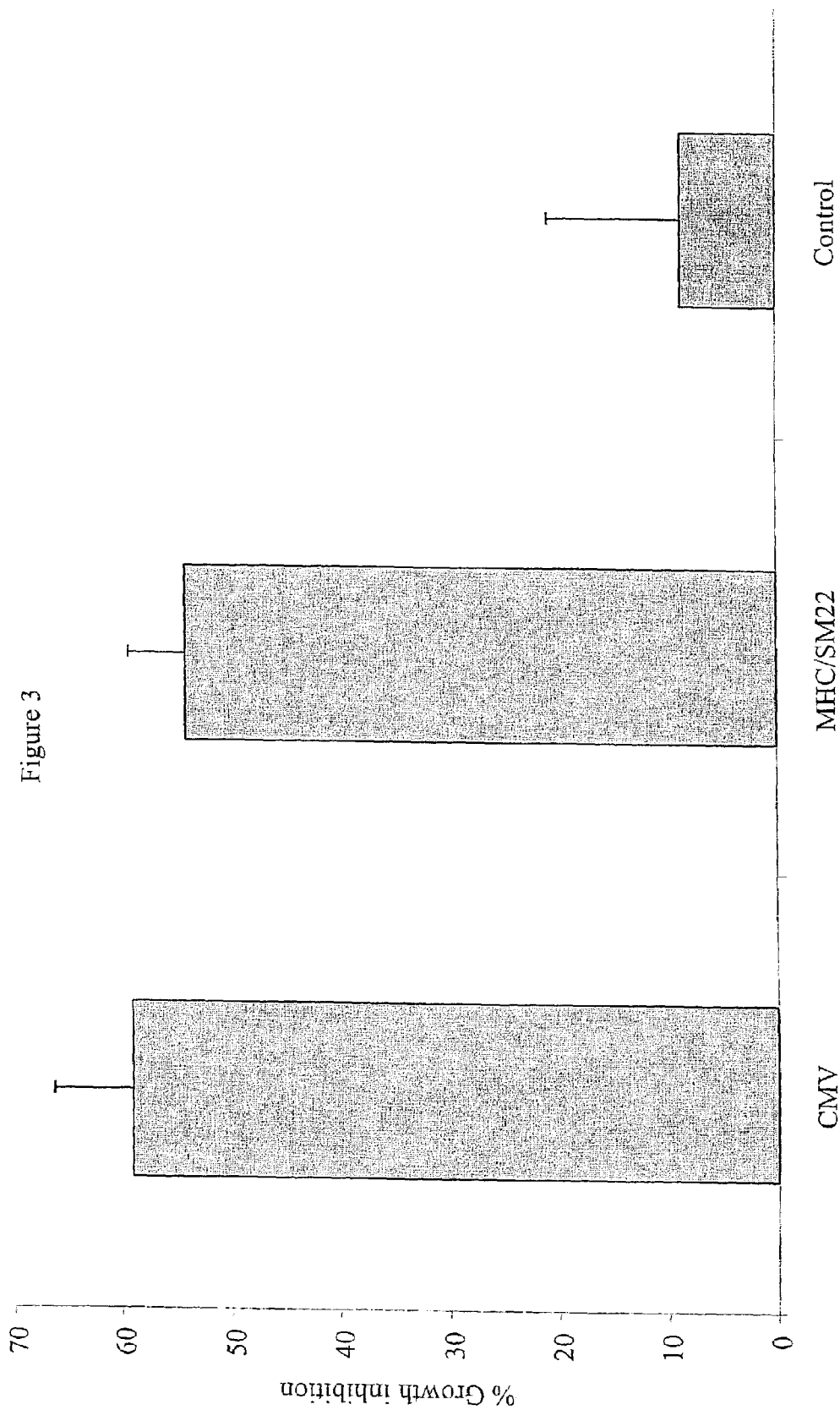

FIG. 3 illustrates the effect of rat gamma IFN to the rat IT15 proliferation. Cells were exposed to AdCMVIFN (, AdSM-MHCenh/SM22IFN (or AdCMVeGFP (control) and counted after 4 days. The antiproliferative effect of the IFN (was evaluated versus non infected cells.

Figure 4:
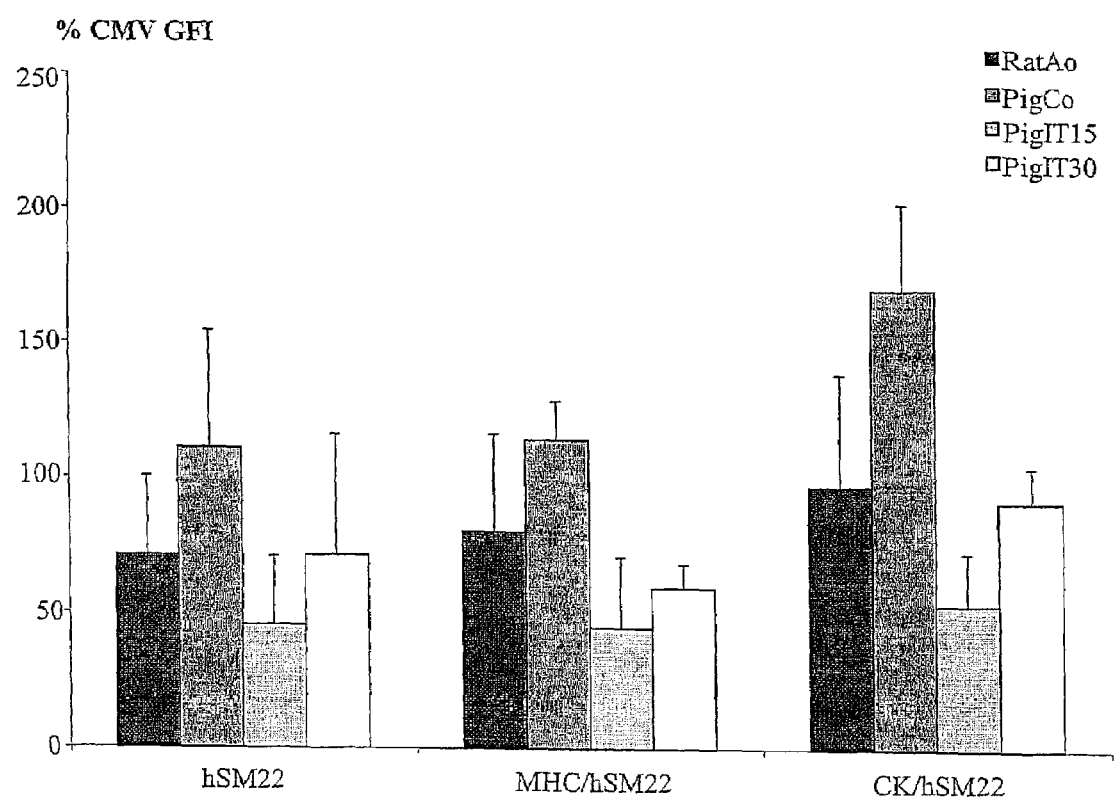

FIG. 4 illustrates the comparison of the vectors containing the human SM22α promoter in SM cells. The SM22α promoter was used alone or in connection with the human creatine kinase enhancer (CK) or the rabbit SM-myosin heavy chain enhancer (MHC). Expression was analysed in rat Ao (black bars), pig Co (dark-grey bars), pig IT15 (light-grey bars) and pig IT30 (white bars). Results are presented as the percentage of the CMV global fluorescence index. Each cell type was exposed to SM22α promoter containing vectors and AdCMVeGFP at the appropriate MOI. The global fluorescence index was determined by flow cytometry at D3.

The following examples serve to illustrate the present invention.

EXAMPLES

Expression Cassettes

The adenoviral genome fragments employed in the different constructs described below are given precisely in accordance with their positions in the nucleotide sequence of the Ad5 genome, as disclosed in Chroboczek et al. (1992, Virol. 186, 280-285).

Standard cloning methods (Sambrook et al., 1989, Laboratory Manual, Cold Spring Harbor Laboratory Press, Cold Spring Harbor N.Y.) were used to generate the following expression cassettes.

AdCMVeGFP was constructed by insertion in the E1 deleted region of the human CMV immediate early enhancer/promoter (Boshart et al., 1985, Cell 41, 521-530) followed by the eGFP sequence (Cormack et al., 1996, Gene 173, 33-38).

AdSM22eGFP, AdSM-MHC/SM22eGFP, AdCK/SM22eGFP were obtained by replacement of the CMV promoter with the 510 bp murine SM22α promoter (−445 to +65 relative to the transcription initiation site) isolated from p445nlz (Moessler et al., 1996, Development 122, 2415-2425). The murine SM22α promoter was then combined with either the human muscle creatine kinase enhancer (CKenh; −919 to −711) (SEQ ID NO: 3; Trask et al., 1988, J. Biol. Chem. 263, 17142-17149) or the rabbit SM-myosin heavy chain enhancer (SM-MHCenh −1332 to −1225; SEQ ID NO: 2) (Kallmeier et al., 1995, J. Biol. Chem. 270, 30949-30957).

These enhancers were isolated by PCR and cloned immediately upstream of the promoter. PCR amplification techniques are known to the person skilled in the art (see for example PCR protocols—A guide to methods and applications, 1990, published by Innis, Gelfand, Sninsky and White, Academic Press). Briefly, the PCR reaction was performed with 1 μg of either human (CKenh) or rabbit (SM-MHCenh) genomic DNA as template, 50 pmol of the following specific primers (CKenh forward 5'-AACCGCTCGAGGGCCAC-CCAGGGCCCCGTG-3' (SEQ ID NO: 4), CKenh reverse 5'-TTCCGCTCGAGCTCGGTCGCCGGGAAAGGAG-3' (SEQ ID NO: 5); SM-MHCenh forward 5'-AACCGCTC-GAGGGCGCGGGGTGCAGGGTGC-3' (SEQ ID NO: 6), SM-MHCenh reverse 5'-TTCCGCTCGAGAATTC-CCAGCG CCGCATACCA-3' (SEQ ID NO: 7), 250 μM dNTP (Sigma, Saint Quentin Fallavier, France) and 2.5 U of Taq-DNA polymerase (Qiagen, Courtaboeuf, France). Amplification was performed at 94° C. for 1 minute, 60° C. for 1 minute, 72° C. for 1 minute for 50 cycles.

AdSM22IFNγ, AdSM-MHC/SM22IFNγ, AdCK/SM22IFNγ were obtained by replacing the eGFP sequence by the rat IFNγ sequence (Genebank accession number AF010466) isolated by RT-PCR. Briefly, total RNA was extracted from rat spleen using TRIZOL Reagent according to the manufacturer's instructions (Sigma). Two μg of total RNA was denatured for 10 minutes at 70° C. in presence of 100 pmol of random primers p(dN)6 (Roche-Diagnostics, Meylan, France) and then reverse transcribed in a final volume of 20 μl for 90 minutes at 37° C. in presence of 200 U of reverse transcriptase (SuperScript II, Life Technologies) and 0.1 mM of each dNTP. The reaction was stopped by heating the mixture for 5 minutes at 95° C. Amplification was performed as mentioned before with the two specific primers (IFNγ forward: 5'-AACCGGAATTCCGGATGAGTGCTA-CACGCCGCGT-3' (SEQ ID NO: 8), IFNγ reverse 5'-TTC-CGGAATTCCGGTCAGCACCGACTCCTTTTCC-3' (SEQ ID NO: 9) (Genebank accession number AF10466).

AdRSVLacZ containing the β-Galactosidase reporter gene driven by the Rous Sarcoma Virus (RSV) 3' long terminal repeat promoter was described previously (Lusky et al., 1998, J. Virol. 72, 2022-2032). AdSM22LacZ was obtained by replacement of the RSV promoter with the 510 bp SM22α promoter.

AdAPEG-1enh/SM22eGFP was obtained by combining the enhancer of the human APEG-1 gene with the murine SM22α promoter. 25 pmol of primer 1 (SEQ ID NO: 10; 5' TCGAGCTTCCCCTCCCCCCAGGGCTGGCTC 3') and primer 2 (SEQ ID NO: 11, 5' CAGCTGAGGCCCCGCACT-GAGCCAGCCCTGGGGGGAGGG-GAAGC 3') were mixed in a final volume of 30 μl. Temperature was increased up to 95° C. during five minutes and the solution was allowed to recover slowly the room temperature. Simultaneously, this operation was performed for primers 3 (SEQ ID NO: 12; 5' AGTGCGGGGCCTCAGCTGGGTCAGC-GAGTGAGTGGGGCTGGCCAGG- CTGAG3') and 4 (SEQ ID NO: 13; 5' TCGACTCAGCCTGGCCAGC-CCCAC- TCACTCGCT GACC 3'). Both couples 1/2 and 3/4 were then hybrized with the same protocol. The final product displays at the 5' end an opened XhoI restriction site and at the 3' end an opened SalI site. They were used to clone the APEG-1 enhancer immediately 5' to the SM22α promoter in a unique SalI site.

The human SM22α promoter was isolated by PCR as described above with human genomic DNA as template and the primers specified in SEQ ID NO: 15 (forward) and 16 (reverse). The amplified fragment digested by SalI and EcoRV was cloned in SalI and EcoRV-restricted AdSM22eGFP in replacement of the murine promoter. The CK and MHC enhancers were combined to the human SM22α promoter as described above.

The intron I of the murine calponin gene containing the enhancer sequence was isolated by PCR performed under the previously described experimental conditions using mouse genomic DNA as template and the primers specified in SEQ ID NO: 17 (forward) and 18 (reverse). The murine calponin enhancer can be inserted downstream (3') of the human SM22α promoter to drive expression of the reporter eGFP gene or the therapeutic gene of interest.

Construction, Production and Titration of Viruses

All viral vectors were constructed as infectious plasmids by homologous recombination in *Escherichia coli* BJ5183 (Hanahan, 1983, J. Mol. Biol. 166, 557-580) as previously described (Chartier et al., 1996, J. Virol. 70, 4805-4810). They were all deleted in the E1 region (nucleotide 459 to nucleotide 3327) and in the E3 region (nucleotide 28593 to nucleotide 30469). Expression cassettes containing a promoter sequence with or without a muscle-specific enhancer followed either by the reporter or the therapeutic gene and by the SV40 polyadenylation signal, were located in E1. Several vectors (see Table 1) contained a chimeric intron inserted between the promoter and the coding region. This intron was generated by combining the splice donor from the human β-globin intron 1 and the splice acceptor from the IgG intervening sequence obtained from the pCI plasmid (Promega, Charbonnieres, France). Two orientations of the expression cassette relative to the adenoviral backbone were evaluated. Adenoviral plasmids were first digested by PacI to release the adenoviral genome and then transfected in the 293 complementation cell line (ATCC CRL1573). Virus propagation, purification and titration of infectious units (iu) by indirect immunofluorescence of the viral DNA binding protein were carried out as described previously (Lusky et al., 1998, J. Virol. 72, 2022-2032). Purified virus was stored in viral storage buffer (1 M sucrose, 10 mM Tris-HCl [pH=8.5], 1 mM $MgCl_2$, 150 mM NaCl, 0.005% [vol/vol] Tween 80).

Cells and Culture Conditions

Primary rat thoracic aortic SMCs and primary porcine coronary artery SMCs were used as SMCs cells. The human pulmonary epithelial A549 and the murine myoblast C2C12 cell lines were used as non-SMC controls. Rat thoracic aorta SMCs were isolated from normal rats (ratAo) and from injured rats 15 days after balloon catheter deendothelialization (ratIT15) by enzymatic digestion as previously described (Orlandi at al., 1994, Arterioscler. Thromb. 14, 982-989). Porcine coronary artery SMCs were isolated from normal pigs (pigCo) and from injured animals 15 or 30 days after stent placement (pigIT15 and pig IT30, respectively) by enzymatic digestion as previously described (Christen et al., 1999, Circ. Res. 85, 99-107). The A549 and C2C12 cell lines were purchased from the American Type Culture Collection (ATCC CCL-185 and CRL-1772, Manassas, Va.). Cells were cultured in DMEM containing 10% FCS (Life Technologies, Cergy-Pontoise, France) except during and after infection where they were grown in 2% FCS containing medium (C2C12 were maintained in 10% FCS to prevent fusion). Human SM cells (Hu Co and Hu Ao) and HUVEC are obtained from Biowhittaker Inc (Walkersville, Md. 21793, USA) and cultured according to the manufacturer's indications.

In Vitro Experiments.

The susceptibility to adenoviral infection of the different cell types was determined using various multiplicities of infection (MOI) of AdCMVeGFP. $2 \times 10^5$ cells/well (except for C2C12: $5 \times 10^4$ cells to prevent fusion) were seeded in 6 well plates (Falcon, Becton Dickinson, Pont de Claix, France) at D0, infected at D1 and harvested at D2. They were fixed in phosphate-buffer saline (PBS) containing 4% formaldehyde for 5 minutes, rinsed twice in PBS, centrifuged at 293 g for 5 minutes and resuspended in 1 ml PBS. The percentage of expressing cells was determined by flow cytometry (FACSCalibur, Becton Dickinson). Further in vitro experiments using eGFP were done at the optimal MOI (e.g. the MOI that allows the highest percentage of infected cells without significant toxicity). No toxic effects were observed for rat, murine and human cells even at MOI corresponding to 100% of infected cells (ratAo: MOI 300; ratIT15: MOI 10; A549: MOI 50 and C2C12: MOI 100). For pig SMCs only 50% of the cells were infected without toxicity (pigCo: MOI 200; pigIT15: MOI 500).

Quantitative analysis of eGFP expression was done by flow cytometry. Briefly, cells were infected as mentioned before but were harvested at D4 to allow eGFP accumulation. The strength of the different regulatory sequences was measured using the Global Fluorescence Index (GFI) calculated as the product of the percentage of GFP positive cells by the mean fluorescence value (Massie et al., 1998, Cytotechnology 28, 53-64). For cell growth inhibition experiments, cells were seeded at a density of $3 \times 10^4$ cells/well in 6 well plates (Falcon, Becton Dickinson) at D0 and infected with AdSM22IFNγ, AdSM-MHC/SM22IFNγ, AdCMVIFNγ at D1. Cultures were maintained in 10% FCS containing medium and cells were counted at D4. A sample of the culture medium was harvested at D3 to quantify the secreted rat IFNγ using an ELISA kit (Quantikine M rat IFNγ, R&D systems, Abingdon, United Kingdom).

In Vivo Gene Transfer into Mice.

Nine-week old female immunocompetent mice (C57BL/6, Iffa-Credo, L'Arbresle, France) were used to study the pattern of expression of SM-specific expression cassettes. At D0, adenoviral vectors were injected intravenously at a dose of $2 \times 10^9$ iu in 100 μl storage buffer. Mice were sacrificed at D3 and organs (liver, lungs, spleen and heart) were harvested and fixed in PBS containing 2% formaldehyde. The eGFP expression was evaluated by fluorescence microscopy.

In Vivo Gene Transfer into Rat Carotids.

Adult male Wistar rats (body weight >400 g) were used for experiments (Iffa-Credo). Anesthesia was induced with intraperitoneal injection of Ketamine (Imalgene, Rhône-Mérieux, Lyon, France) and Acepromazin (Vetranquil 0.5%, Sanofi, Libourne, France) in doses of 23.1 and 3.84 mg/kg respectively. Animals were anticoagulated with intravenous injection of 200 U/kg of human heparin (Choay, Sanofi Winthrop, Gentilly, France). The left common carotid artery was surgically exposed and an arteriotomy was made on the left external carotid artery. Deendothelialization was achieved by three passages of a 2F Fogarty balloon catheter (Baxter, Maurepas, France) filled with 0.2 ml air. A segment of the carotid of 1 cm length was isolated with microsurgical clamps and a 24-gauge catheter was introduced through the arteriotomy. The segment was flushed with 0.2 ml NaCl 0.9% and 50 μl of adenoviral solution ($2 \times 10^9$ iu) was infused. The solution was allowed to dwell in the carotid for 5 minutes during which the carotid segment remained distended. The solution was withdrawn, the external carotid artery was ligated and blood flow was reestablished through the common and the internal carotid arteries. Rats were sacrificed at different time points according to the different experiments. After lethal pentobarbital injection and cannulation of the heart, vessels were perfused with 1×PBS solution and perfusion-fixed either with 2% or 4% formaldehyde in PBS at normal blood pressure. Then, carotids were excised and treated for the different histological analyses.

Histological and Immunocytochemical Analysis

Immunohistochemical staining for SM22α was performed on 4 μm-thick sections from 4% formaldehyde-fixed and paraffin-embedded carotids. Sections were deparaffinized and immersed in distillated water containing 3% $H_2O_2$ for 10 minutes. Sections were then incubated for 1 hour at room temperature with the E-11 SM22α mouse monoclonal antibody (kindly provided by Dr. S. Sartore; Faggin et al., 1999, Arterioscler. Thromb. Vasc. Biol. 19, 1393-1404) at a dilution of 1:100. The secondary antibody was a biotinylated goat anti-mouse used at a dilution of 1:100. The presence of SM22α was revealed by means of the streptavidin-biotin-complex peroxidase method (LSAB kit, Dako, Trappes, France). Slides were counterstained with hematoxylin. For β-galactosidase activity, vessels fixed in 2% formaldehyde were rinsed in PBS and incubated for 24 hours at 37° C. in 5 mM $K_3Fe(CN_6)$, 5 mM $K_4Fe(CN_6)$, 2 mM $MgCl_2$, 1 mg/ml 5-bromo-4.chloro.3-indolyl-β-D-galactopyranoside (X-gal). Carotids were then rinsed in PBS, post-fixed in 5% formamide/PBS for 24 hours at 4° C., dehydrated and embedded in paraffin. Five μm sections were examined for blue nuclear staining. For morphological analyses, arteries fixed in 4% formaldehyde were embedded in paraffin. Five μm sections were stained with hematoxylin and eosin. The medial and intimal area as well as cell number were evaluated by image analysis (Scion Image).

Virus DNA Analysis

Total DNA was extracted from organs as described previously (Lusky et al., 1998, J. Virol. 72, 2022-2032). DNA (10 μg) was digested by SalI and analyzed by Southern blot, using a $^{32}P$ labeled restriction fragment corresponding to the entire eGFP cDNA. The quality and quantity of DNA were monitored by ethidium bromide staining of the gels prior to transfer.

Statistical Analysis

All results are expressed as mean values ±SEM. For statistical evaluation, the results were analysed by means of t-test. Differences were considered statistically significant at values of $P<0.05$.

Example 1

Functionality and Specificity of the Murine SM22∀ Promoter in the Adenoviral Context As summarized in Table 1, four adenoviral constructs were generated by insertion of an eGFP expression cassette driven only by the SM22α promoter in the E1-deleted region of human adenovirus serotype 5. To prevent and/or detect interactions with adenoviral internal regulatory elements, cassettes were cloned in each of the two orientations. The effect of an intron liable to stabilize the mRNA was also tested.

TABLE 1

| Promoter | Reporter gene | Intron | Orientation | Adenovirus |
|----------|---------------|--------|-------------|------------|
| SM22α | EGFP | + | Sense | AdSM22eGFP |
| SM22α | EGFP | − | Sense | AdSM22(−)eGFP |
| SM22α | EGFP | + | Antisense | AdSM22AseGFP |
| SM22α | EGFP | − | Antisense | AdSM22(−)AseGFP |

A. Susceptibility of SMC and Non-SMC Cell Lines to Adenoviral Infection.

The susceptibility of SMCs derived from rat aortas and pig coronary arteries and of A549 control cells to adenovirus infection was determined by infection with Ad-CMV/eGFP at MOI ranging from 1 to 1000. No more than 50% of pig cells could be infected with non toxic MOI. For example, between MOI500 and MOI700 no significant changes could be observed in the number of pig IT15 infected cells with 50±2% and 56±2%, respectively. A great variability in SMC infection was observed since the MOI corresponding to the optimal infection (100% for rat cells and 50% for pig cells) varied from 10 for rat neointimal cells to 500 for pig IT15 cells.

According to the different susceptibilities of infection, cells were infected with the four adenoviral vectors and eGFP expression was evaluated by fluorescence microscopy. When comparing the four constructs driven by the mouse SM22α promoter, expression levels were not significantly different in terms of strength and specificity. Indeed, expression was detected in all SMCs whereas little or no expression was obtained in A549. AdSM22eGFP was then chosen for further in vitro experiments. It contains in sense-orientation with respect to the adenoviral backbone the eGFP expression cassette driven by the SM22α promoter and equipped with an intron.

B. Effect of Cell Differentiation on the SM22α Promoter Activity.

A549, rat Ao and rat IT15 were infected with AdSM22eGFP or the control Ad-CMV/eGFP at MOI corresponding to 50% and 100% infected cells at day 0. These cells were then cultured for three days in 2% (differentiated state) or 10% (proliferative state) FCS-containing medium to study the effect of cell differentiation on SM22α-driven eGFP expression. As expected, eGFP expression was detected in all cell types infected with Ad-CMV/eGFP albeit at different intensities. When infected with AdSM22eGFP, the non-SM cell line (A549) lacked eGFP fluorescence. On the other hand, in rat Ao, a strong fluorescence was observed, especially in low serum conditions with a decrease in high serum containing medium. In rat IT15, the fluorescence was present only in low serum conditions. These data confirm that SM22α-driven expression remains SMC-specific in the adenoviral vector context. The absence or decrease of the fluorescence in the presence of a high concentration of serum suggests that in SMCs, the SM22α promoter is differentially regulated with respect to at least the cellular differentiation state.

C. In Vitro Quantification of the SM22α Promoter Activity.

The eGFP expression driven by the mouse SM22α promoter was compared quantitatively to eGFP expression levels obtained with the strong CMV promoter/enhancer in SMCs of two species (pig and rat), either normal (aortic Ao and coronary Co) or restenotic (IT15), and in non SMCs (A549). The cells were seeded at high density and infected the next day at MOI corresponding to the optimal infection (pig 50%, rat 100%). The level of eGFP expression (fraction of cells expressing eGFP and its fluorescence intensity) was analyzed by flow cytometry after three days. The relative strength of the CMV and SM22α promoters was compared using the global fluorescence index and is shown in FIG. 1.

The global fluorescence index of CMV driven expression was arbitrarily set at 100% in every cell type tested. Concerning the SM22α promoter, a weak eGFP expression was observed in A549 cells (2.0% of the CMV driven expression). In all rat and pig SMCs, the mouse SM22α promoter lead to higher eGFP expression ranging from 5.7% in rat Ao, 6% in pig Co, 8.8% in rat IT15 to 15.3% in pig IT15.

D. Influence of MOI on the SM22α-Driven Expression

It has been suggested that the viral load may influence both the cell physiology and the promoter activity, as shown in human VSMCs (Cleesham et al., 1998, Gene Ther. 5, 174-180) or in established cell lines like HepG2 (Loser et al., 1998, J. Virol. 72, 180-190), due to a stimulation of NFκB factor. Therefore, the CMV promoter like many other promoters is dependent on the NFκB presence to be fully active.

To determine the effect of high viral loads on transgene expression, rat Ao, rat IT15, pig Co and pig IT15 were infected at different MOI starting from the viral dose which allows optimal infection (respectively MOI 10, 50 and 100 in rat IT15, MOI 300 and 500 in rat Ao, MOI 200, 300 and 400 in pig Co and MOI 500, 600 and 700 in pig IT15).

In rat Ao and pig Co, increasing the viral dose (respectively from MOI 300 to 500 and from MOI 200 to 400) resulted in a 5 fold increase of the SM22α promoter driven expression while the CMV-driven expression remained unchanged. In rat IT15, the eGFP expression increased with the viral dose for both CMV and SM22α promoter but in different proportions. A 10-fold increase in viral concentration (MOI 10 to 100) gave a 3 fold gain in fluorescence with the SM22α promoter versus 8 with the CMV. Similarly, in pig IT15, the fluorescence increased more quickly when eGFP is controlled by the CMV promoter than to the SM22α promoter. Increasing the MOI from 500 to 700 did not significantly change the SM22α-related expression when expression was 2-fold stronger with the CMV promoter.

The higher proliferative state of neointimal cells (IT15 cells) compared to medial cells (Ao and Co) seems to influence the regulation of viral and cellular promoters. This may be due to major differences in the presence of the necessary transcription factors. Therefore, strict comparison the SM22α and CMV promoters requires analysis at a MOI precisely corresponding to optimal infection and under conditions where superinfection is avoided.

Example 2

In Vivo Evaluation of the SM22α Promoter

A. Evaluation of the SM22α Promoter Specificity in Mice.

The dissemination of adenoviral vectors in the blood circulation following an intravenous or intraarterial administration is a major problem, especially when they are used to deliver potentially harmful therapeutic genes (cytotoxic, for example). To verify that SM22α-driven expression did not occur in one of the main adenovirus natural target organs (e.g. liver, lung, spleen and heart), the four adenoviral constructs containing the SM22α promoter (see Table 1) were injected into C57Bl6 immunocompetent mice. The Ad-CMVeGFP vector and Tris-HCl injections were used as positive and negative controls, respectively. Four mice were injected intravenously with $2.10^9$ iu of each construct and eGFP expression was determined by fluorescence microscopy examination of the different organs three days later. Southern blot analysis was performed with DNA extracted from the abovementioned organs using an adenovirus specific probe. Similar viral DNA quantities were detected in all mice, indicating a correct infection.

The four mice injected with Ad-CMV/eGFP showed significant fluorescence in all organs tested whereas the animals injected with the virions containing the SM22α promoter did not show any fluorescence, which confirms the tissue-specificity of the mouse SM22α promoter. This specificity remained independent of the expression cassette orientation indicating that adenoviral sequences did not interfere with the promoter specificity in vivo.

B. Evaluation of the SM22α Promoter in Rat Carotid Injury Models.

To assess the therapeutic capacity of the adenoviral vectors, two adenoviral vectors containing the LacZ bacterial gene under the control of either the RSV (Ad-RSV/LacZ) or the SM22α (Ad-SM22/LacZ) promoter were generated and packaged into viral particles as described in Example 1. $2.10^9$ iu were instilled for 5 minutes in the carotid isolated segment of rats models having induced carotid injury. After 7 days, the Ad-RSV/LacZ and Ad-SM22/LacZ infected carotids were stained for β-galactosidase.

All examined vessels infected with both viruses showed a blue staining in the media with rare blue cells in the nascent neointima. Infected medial cells were generally surrounded by the neointimal formation. These results confirm that Ad-SM22/LacZ is capable of infecting the SMC target cells, even in pathological conditions.

Altogether, these data indicate that the SM22α promoter in the adenoviral context leads to a SMC-specific expression of reporter genes (eGFP and β-galactosidase encoding genes) in vitro and in vivo. When tested in rat and pig SM cells from medial and neointimal origins, this promoter showed expression levels ranging from 6 to 15% of the strong viral CMV enhancer/promoter.

Example 3

Functionality and Specificity of the Chimeric SM22α Promoter in the Adenoviral Context A. In Vitro Quantification of the Chimeric SM22α Promoters Activity The strength and specificity of expression of the chimeric promoters combining SM22α promoter with the CK or the MHC enhancer, were first tested in vitro with the eGFP encoding gene as a reporter gene. The analysis of the global fluorescence index was done as before to evaluate the specificity of the constructs and to compare them with the strong CMV enhancer/promoter in normal (rat Ao), restenotic (rat IT15) SM cells and non-SM cells (A549). To facilitate the comparison, the global fluorescence index of CMV-driven expression was arbitrarily set to 100% in every cell type tested. The comparative data are shown in FIG. 2.

Non-specific expression levels in A549 are reduced with both chimeric constructs compared to the mouse SM22α promoter alone (each 0.5% versus 2% in A549). The presence of the CK enhancer increased eGFP expression by about 3 fold in rat Ao and rat IT15 with 15.8% and 21.3% of the CMV related expression, respectively. The vectors having incorporated the MHC enhancer gave even higher expression levels in both types of SMCs with 16.9% of the CMV expression in rat Ao and 23.5% in rat IT15.

Due to the skeletal muscle origin of the CK enhancer, the chimeric vectors were also tested in murine myoblasts using the C2C12 cell line. Suprisingly, the intensity of eGFP fluorescence was similar with all constructs tested (SM22α promoter alone or in combination with CK or MHC enhancer) and in the same range as the intensity observed in the A549 cell line (about 1.7% of the CMV promoter). As a control, eGFP expression driven by the CMV enhancer/promoter is observed at high levels. Thus, the skeletal-specificity of the CKenh is lost when combined with the mouse SM22α promoter to the advantage of SMC specificity. These data confirm the SMC specificity of the MHCenh/SM22α and CKenh/SM22α chimeric vectors.

B. Effect of Cell Differentiation on Chimeric Vectors Related Expression.

The constructs containing SM22α, alone or in combination with the CK or the MHC enhancer, were tested in rat Ao cultured in the presence of 2 or 10% FCS to determine the effect of cell proliferation/differentiation on the expression. All constructs were downregulated in the presence of high concentrations of serum like the CMV promoter/enhancer. Thus, chimeric constructs combining the muscle-specific enhancers CK and MHC with the mouse SM22α promoter followed the natural regulation of the differentiation markers (SM22α, SM-MHC, α actin) and are more active in differentiated cells.

C. In Vitro Evaluation of Adenoviral Vector Expressing Rat IFNγ

Adenoviral vectors expressing the rat IFNγ gene driven by the SM22α promoter combined to the MHC enhancer were tested for their ability to prevent SMC proliferation in rat IT15 cells cultured in a 10% FCS containing medium (to enhance their proliferation). Rat IT15 infection was also performed with CMVpro/IFNγ adenoviral vectors (positive controls) and with a CMVpro/eGFP adenoviral vector (negative control). The results shown in FIG. 3 are expressed as the percentage of growth inhibition at D4 after infection.

The growth inhibition of the rat cells obtained with the adenoviruses expressing IFNγ under the control of both chimeric promoters is in the same range as or slightly higher than the one generated with the viruses containing the CMV promoter/enhancer (54% versus 59%). Infection with the negative control (CMVpro/eGFP) led to a faint growth inhibition statistically not significant compared with non infected cells.

Supernatants of infected cells were harvested at day 3 and tested by ELISA to determine the rat IFNγ concentration. IFNγ concentration obtained with the chimeric MHCenh/SM22α promoter was evaluated to 9 ng/ml versus 31 ng/ml with the CMV promoter/enhancer Example 4

In Vivo Evaluation of Chimeric Vectors in Mice

A. Evaluation of the SM22α Promoter Specificity in Mice

The eGFP expression in liver, lung, spleen and heart was checked as described in Example 2 by injecting in the tail vein of C57B16 immunocompetent mice $2 \times 10^9$ iu of the adenoviruses containing SM22α alone or in combination with the CK or the MHC enhancer, Ad-CMV/eGFP (positive control), or Tris-HCl (negative control). A total of four animals was tested per construct.

The four mice injected with Ad-CMV/eGFP showed a significant fluorescence in all organs tested whereas all the mice injected with the SM22α containing vectors did not show any fluorescence.

The capability of the adenovirus containing the chimeric construct of CK enhancer linked to SM22α to direct gene expression in non-smooth muscle cells was also studied. $2 \times 10^9$ iu of AdCKenh/SM22eGFP were injected by intramuscular route (in the tibialis anterior muscle) to C57B16 immunocompetent mice. AdCMVeGFP was used as a positive control. Fluorescence induced by eGFP expression was evaluated by microscopic observation of muscle sections. The mice injected with AdCKenh/SM22eGFP showed no fluorescence whereas all the animals treated with Ad-CMV/eGFP showed an intense fluorescence of the skeletal fibers.

These results confirm the SMC-restricted specificity of the chimeric constructs of the present invention.

B. Evaluation of the Chimeric Promoter/Enhancer in the Rat Injury Model.

The antiproliferative effect of the rat IFNγ driven by the SM22α promoter combined to the MHC enhancer was evaluated in the rat carotid balloon injury model, as previously described in Example 2. $2 \times 10^9$ iu of adenoviruses were injected locally in the rat injured carotid. Control rats received the CMVpro/IFNγ containing adenoviruses.

When driven either by the MHCenh/SM22α promoter or by the CMV promoter, the rat IFNγ inhibited in part the formation of the neointimal thickening in the rat carotid model. This inhibition analyzed 14 days after injury reached 35% compared to controls infused with a control adenovirus lacking the expression cassette while medial areas remained the same in all groups.

These data show that chimeric constructs having specific enhancers (MHC or CK) combined to the mouse SM22α promoter led to a significant stronger specific expression reaching up to 25% of the CMV promoter/enhancer expression in vitro. In vivo, the expression was restricted to arterial SMCs with no detectable signal in liver, spleen, lung, heart and skeletal muscle. Chimeric vectors carrying the rat IFN (were efficient to inhibit the rat aortic and IT15 cell proliferation in vitro. Moreover, this growth inhibition was as strong as with the CMV enhancer/promoter. Taken together, these data suggest that the chimeric enhancer/promoters constructs of the invention are useful for the specific expression of therapeutic genes in vascular proliferative diseases.

Example 5

Functionality and Specificity of the Expression Cassettes Supplied with the Human SM22α Promoter in the Adenoviral Context A. In Vitro Quantification of the Chimeric Human SM22α Promoter Activity The strength and specificity of expression of the human SM22α promoter or chimeric promoters combining the human SM22α promoter with CK or MHC enhancer, were first tested in vitro with the eGFP encoding gene as a reporter gene. The analysis of the global fluorescence index was done as before to evaluate the specificity of the constructs and to compare them to the strong CMV enhancer/promoter in normal (ratAo, pigCo, huAo, huCo), restenotic (pigIT15, pigIT30) SM cells and non SM HUVEC cells. To facilitate the comparison, the global fluorescence index of CMV driven expression was arbitrarily set at 100% in every cell type tested. The comparative data concerning rat and pig cells are shown in FIG. 4.

The expression driven by the human SM22α (hSM22α) promoter in ratAo was strong and reached about 71% of the CMV-related expression. This expression was only weakly increased by the addition of the MHC enhancer or the CK enhancer with 80% and 97% of the CMV-related expression, respectively. Similar results were observed in pigCo with 110%, 114% and 170% of the CMV-related expression when eGFP expression was driven by the hSM22α promoter, the SM-MHC/hSM22α promoter and the CK/hSM22α promoter, respectively. In pigIT15 and pigIT30, the expression driven by the hSM22α promoter is, respectively, approximately 50% (pigIT15) and 70% (pig IT30) of that obtained with the CMV promoter/enhancer. The expression level remains in the same range in both cells when the hSM22α promoter is associated with the MHC enhancer and slightly increased in association with the CK enhancer.

As expected, only a background of eGFP expression could be detected in non-SM HUVEC cells with all hSM22α promoter-containing constructs (less than 0.05% of the CMV-related expression).

In human cells (HuAo and HuCo), eGFP expression driven by the three hSM22α-containing vectors was also determined as SMC-specific although lower levels were obtained (approximately 5% of the CMV-related expression).

B. Impact of Cell Culture Conditions on hSM22α Promoter Activity.

The question was addressed as to whether cell culture conditions could affect the human SM22α promoter activity in human cells. Therefore, the impact of cell confluence and serum concentration on these cells and on the subsequent hSM22α promoter activation was evaluated. Human coronary cells were seeded in a 2% or a 10% FCS containing medium at $5.10^4$ or $2.10^5$ cells per well in 6 well/plates.

In human coronary cells infected at $2\times10^5$ cell density and cultured in the presence of 2% serum, eGFP expression levels was determined as 1.5%, 2.5% and 4% of the CMV-related expression when the eGFP gene was placed under the control of the hSM22α promoter, the MHC/hSM22α promoter and the CK/hSM22α promoter, respectively. Similar results were observed in huCo infected at $5\times10^4$ density with 2%, 5.5% and 5.5%, respectively, of the CMV-related expression. Higher expression levels (increased by a factor of 2.5 to 4) were obtained when the human coronary cells were cultured in 10% serum-containing medium. Cell infection at $2\times10^5$ density resulted in 4%, 6% and 11% of eGFP expression with the hSM22α, MHC/hSM22α and CK/hSM22α promoter, respectively, whereas expression reached 7.5%, 17.5% and 22%, respectively, with the same constructs when infection was carried out at low cell density ($5\times10^4$).

In summary, eGFP expression driven by the hSM22α promoter-containing vectors was constantly stronger at lower concentration of cells ($5.10^4$). Moreover, the presence of serum significantly increased the expression driven by the three hSM22α-containing promoters. As a result, expression levels obtained with the hSM22α chimeric promoters reached about 20% of the CMV when human SM cells were infected at low confluence and cultured in high serum concentration.

Example 6

In Vivo Evaluation of the Human SM22α Promoter

A. Evaluation of the Human SM22α Promoter Specificity in Mice.

To verify that hSM22α-driven expression did not occur in one of the main adenovirus natural target organs (e.g. liver, lung, spleen and heart), adenoviral constructs containing the hSM22α promoter alone or in combination with the MHC or CK enhancer were injected into C57B1/6 immunocompetent mice. The Ad-CMVeGFP vector and Tris-HCl injections were used as positive and negative controls, respectively. Four mice were injected intravenously with $2.10^9$ iu of each construct and eGFP expression was determined by fluorescence microscopy examination of the different organs three days later, as described above.

The four mice injected with Ad-CMV/eGFP showed significant fluorescence in all organs tested whereas the animals injected with the virions containing the hSM22α promoter did not show any fluorescence, which confirms the SMC-specificity of the human SM22α promoter.

B. Evaluation of the MHC/hSM22α Promoter in Rat Carotid Injury Models.

To assess the capacity of the MHC/hSM22α-containing adenoviral vector in SMCs in vivo, vectors containing the eGFP under the control of either the CMV (AdCMVeGFP) or the MHC/hSM22α (AdMHC/hSM22eGFP) promoter were generated and packaged into viral particles as described previously. $2.10^9$ iu were instilled for 5 minutes in the carotid isolated segment of rats models having induced carotid injury. After 3 days, the AdCMVeGFP and AdMHC/hSM22eGFP infected carotids were harvested, fixed in PBS/2% formaldehyde and analyzed by fluorescence microscopy. Both AdCMVeGFP- and AdMHC/hSM22eGFP-infected vessels showed a significant fluorescence. These results confirm that the MHC/hSM22α promoter is capable of driving the eGFP expression in SMCs while it is silent in non-SMCs.

Altogether, these data indicate that the hSM22α-containing promoters in the adenoviral context lead to a SMC-specific expression of a reporter gene in vitro and in vivo. When tested in rat, pig and human SM cells from medial and neointimal origins, these promoters showed expression levels ranging from 5 to 170% of the strong viral CMV enhancer/promoter.

The invention claimed is:

1. A chimeric construct comprising at least (i) a smooth muscle cell (SMC)-specific promoter operably linked with at least (ii) a muscle-specific enhancer;
   wherein the promoter and enhancer originate from different genes, different species, or different genes and species;
   said promoter is selected from the group consisting of
   a SMC-specific promoter comprising the 445 base pair region of the mouse SM22α promoter set forth in SEQ ID NO: 1 from positions 1 to 445; and,
   a SMC-specific promoter comprising the 445 base pair region of the human SM22α promoter set forth in SEQ ID NO: 14 from positions 1 to 445;
   and wherein said muscle-specific enhancer is selected from the group consisting of enhancers of the genes encoding: a rabbit myosin and a human creatine kinase.

2. The chimeric construct according to claim 1, wherein said muscle-specific enhancer is from the rabbit myosin heavy chain encoding gene.

3. The chimeric construct according to claim 2, wherein said muscle-specific enhancer comprises the sequence of nucleotides located 1332 to 1225 nucleotides upstream of the transcription initiation site of the rabbit myosin heavy chain encoding gene as set forth in SEQ ID NO: 2.

4. The chimeric construct according to claim 1, wherein said muscle-specific enhancer comprises the sequence of nucleotides located 919 to 711 nucleotides upstream of the transcription initiation site of the human creatine kinase gene as set forth in SEQ ID NO: 3.

5. An expression cassette comprising a gene of interest placed under the control of a chimeric construct according to claim 1, allowing its expression in a target cell.

6. The expression cassette according to claim 5, wherein said gene of interest encodes a polypeptide having growth suppressive activities on SMCs.

7. The expression cassette according to claim 6, wherein said polypeptide is selected from the group consisting of IFNβ, IFNγ, nitric oxide synthase eNOS, Fas ligand, heme oxygenase, interleukin-10 and heparin-binding VEGF.

8. The expression cassette according to claim 5, wherein said expression cassette further comprises one or more exons or portions of exons.

9. The expression cassette according to claim 8, which comprises the portion of the first non-coding exon of the mouse SM22α gene extending from position 1 to position 65 downstream from its transcription initiation site as set forth in SEQ ID NO: 1 from position 446 to position 510 or the portion of the first non-coding exon of the human SM22α gene extending from position 1 to position 63 downstream from its transcription initiation site as set forth in SEQ ID NO: 14 from position 446 to position 508.

10. A vector comprising the expression cassette according to claim 5.

11. The vector according to claim 10, wherein said vector is a viral vector derived from a virus selected from the group consisting of herpes viruses, cytomegaloviruses, foamy viruses, lentiviruses, Semliki forrest virus, AAV (adeno-associated virus), poxviruses, retroviruses and adenoviruses.

12. The vector according to claim 11, wherein said viral vector is a replication-defective adenoviral vector.

13. A method for the preparation of viral particles allowing the SMC-specific expression of a gene of interest in a target cell, said method comprising the steps of:
   a) introducing the viral vector of claim 11 in a permissive cell line;
   b) culturing the permissive cell line obtained in step a) for an appropriate period of time and under suitable conditions to allow the production of said viral particles;
   c) recovering said viral particles from the cell culture; and
   d) optionally, purifying the recovered viral particles.

14. A viral particle comprising the vector according to claim 10.

15. An isolated vascular smooth muscle cell comprising the expression cassette according to claim 5.

16. A method for specific expression of a gene of interest in SMCs in vitro comprising introducing the expression cassette according to claim 5 into said SMCs.

* * * * *

SEQUENCE LISTING

```
<160> NUMBER OF SEQ ID NOS: 18

<210> SEQ ID NO 1
<211> LENGTH: 510
<212> TYPE: DNA
<213> ORGANISM: mouse
<220> FEATURE:
<221> NAME/KEY: promoter
<222> LOCATION: (1)..(445)

<400> SEQUENCE: 1
ctgcagtcaa gactagttcc caccaactcg attttaaagc cttgcaagaa ggtggcttgt      60
ttgtcccttg caggttcctt tgctcgggcc aaactctaga atgcctcccc ctttctttct     120
cattgaagag cagacccaag tccgggtaac aaggaagggt ttcagggtcc tgcccataaa     180 aggttttttcc cggccgccct cagcaccgcc ccgccccgac ccccgcagca tctccaaagc     240
```

-continued

```
atgcagagaa tgtctccggc tgcccccgac agactgctcc aacttggtgt ctttccccaa    300
atatggagcc tgtgtggagt gagtggggcg gcccggggtg gtgagccaag cagacttcca    360
tgggcaggga ggggcgccac ggggcggcag aggggtgaca tcactgccta ggcggccttt    420
aaacccctca cccagccggc gccccggccc gtctgcccca gcccagacac cgaagctact    480
ctccttccag tccacaaacg accaagcctt                                     510
```

<210> SEQ ID NO 2
<211> LENGTH: 112
<212> TYPE: DNA
<213> ORGANISM: RABBIT

<400> SEQUENCE: 2

```
gcgcggggtg cagggtgccc tcccccgcac cggccgagcc gagaggccgc gaggcaccat     60
atttagtcag cgggagcggg cagccccggg ctggtatgcg gcgctgggaa tt            112
```

<210> SEQ ID NO 3
<211> LENGTH: 210
<212> TYPE: DNA
<213> ORGANISM: Homo sapiens

<400> SEQUENCE: 3

```
ggccacccag ggccccgtgg ctgcccttgt aaggaggcga ggcccgagga cacccgagac     60
gcccggttat aattaaccag gacacgtggc gaaccccccct ccaacacctg ccccgaacc    120 cccccatacc cagcgcctcg ggtctcggcc tttgcggcag aggagacagc aaagcgccct    180
ctaaaaataa ctcctttccc ggcgaccgag                                     210
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer CK
      enhancer forward

<400> SEQUENCE: 4

```
aaccgctcga gggccaccca gggccccgtg                                      30
```

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:primer CK
      enhancer reverse

<400> SEQUENCE: 5

```
ttccgctcga gctcggtcgc cgggaaagga g                                    31
```

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:primer
      SM-MHC enhancer forward

<400> SEQUENCE: 6

```
aaccgctcga ggcgcggggt gcagggtgc                                       29
```

```
<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:primer
      SM-MHC enhancer reverse

<400> SEQUENCE: 7
ttccgctcga gaattcccag cgccgcatac ca                                    32

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:primer IFN g
      forward

<400> SEQUENCE: 8
aaccggaatt ccggatgagt gctacacgcc gcgt                                  34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence:primer IFN g
      reverse

<400> SEQUENCE: 9
ttccggaatt ccggtcagca ccgactcctt ttcc                                  34

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:primer
      APEG-1 enhancer forward

<400> SEQUENCE: 10
tcgagcttcc cctccccca gggctggctc                                        30

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence:primer
      APEG-1 enhancer reverse

<400> SEQUENCE: 11
cagctgaggc cccgcactga gccagccctg gggggagggg aagc                       44

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence:primer
      APEG-1 enhancer forward

<400> SEQUENCE: 12 agtgcgggc ctcagctggg tcagcgagtg agtggggctg gccaggctga g                51
```

```
<210> SEQ ID NO 13
<211> LENGTH: 37
<212> TYPE: DNA
<213> ORGANISM: Homo sapiens

<400> SEQUENCE: 13
tcgactcagc ctggccagcc ccactcactc gctgacc                              37

<210> SEQ ID NO 14
<211> LENGTH: 508
<212> TYPE: DNA
<213> ORGANISM: Homo sapiens
<220> FEATURE:
<221> NAME/KEY: promoter
<222> LOCATION: (1)..(445)
<220> FEATURE:
<221> NAME/KEY: exon
<222> LOCATION: (446)..(508)

<400> SEQUENCE: 14
aggagagggt ggctggtttg tccccacaaa cccctgggat tcccggctcc ccagccccctt     60 gccccctctct ccagccagac tctattgaac tccccctctt ctcaaactcg ggccagaga    120 acagtgaagt aggagcagcc gtaagtccgg gcagggtcct gtccataaaa ggctttttccc   180 gggccggctc cccgccggca gcgtgccccg ccccggcccg ctccatctcc aaagcatgca    240
gagaatgtct cggcagcccc ggtagactgc tccaacttgg tgtctttccc caaatatgga    300
gcctgtgtgg agtcactggg ggagccgggg gtggggagcg gagccggctt cctctagcag    360 ggaggggggcc gaggagcgag ccagtggggg aggctgacat caccacggcg gcagcccttt    420 aaaccccctca cccagccagc gcccc atc ctg tct gtc cga acc cag aca caa   472 gtc ttc act cct tcc tgc gag ccc tga gga agc ctt                     508

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence : primer
      hSM22a (forward)

<400> SEQUENCE: 15
aacgcgtcga caggagaggg tggctggttt gt                                   32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence : primer
      hSM22a (reverse)

<400> SEQUENCE: 16
aacgcgtcga caggagaggg tggctggttt gt                                   32

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence : primer
      calponin enhancer (forward)

<400> SEQUENCE: 17
ataattgata tcaacaaggt aaggctggaa gga                                  33
```

```
<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence : primer
      calponin enhancer (reverse)

<400> SEQUENCE: 18
ttcccaagct tctcgagggc cagctgagga ggagaca                                    37
```